(12) United States Patent
Wyeth et al.

(10) Patent No.: US 11,920,997 B2
(45) Date of Patent: Mar. 5, 2024

(54) OPTICAL PRESSURE MEASUREMENT DEVICES, METHODS, AND SYSTEMS

(71) Applicant: NxStage Medical, Inc., Lawrence, MA (US)

(72) Inventors: Mark T. Wyeth, Andover, MA (US); James M. Brugger, Newburyport, MA (US); Adam G. McDermott, Acton, MA (US)

(73) Assignee: NxStage Medical, Inc., Lawrence, MA (US)

( * ) Notice: Subject to any disclaimer, the term of this patent is extended or adjusted under 35 U.S.C. 154(b) by 155 days.

(21) Appl. No.: 17/439,119

(22) PCT Filed: Mar. 12, 2020

(86) PCT No.: PCT/US2020/022341
§ 371 (c)(1),
(2) Date: Sep. 14, 2021

(87) PCT Pub. No.: WO2020/190635
PCT Pub. Date: Sep. 24, 2020

(65) Prior Publication Data
US 2022/0146351 A1    May 12, 2022

Related U.S. Application Data

(60) Provisional application No. 62/818,962, filed on Mar. 15, 2019.

(51) Int. Cl.
*G01L 7/08* (2006.01)
*A61M 1/36* (2006.01)

(52) U.S. Cl.
CPC ............ *G01L 7/086* (2013.01); *A61M 1/3639* (2013.01)

(58) Field of Classification Search
CPC . G01L 19/147; G01L 9/0072; G01L 19/0645; G01L 19/0084; G01L 13/025;
(Continued)

(56) References Cited

U.S. PATENT DOCUMENTS 3,418,853 A    12/1968    Curtis
4,576,181 A     3/1986    Wallace et al.
(Continued)

FOREIGN PATENT DOCUMENTS

EP       1582852 A2    10/2005
WO    2012166980 A2    12/2012
WO    2018141705 A1     8/2018

OTHER PUBLICATIONS

1 European Search Report for European Application No. 20774779.1 dated Nov. 18, 2022.
(Continued)

*Primary Examiner* — Andre J Allen
(74) *Attorney, Agent, or Firm* — Potomac Law Group, PLLC

(57) ABSTRACT

A pressure measurement system includes a pressure pod with two chambers separated by a diaphragm such that a deformation/movement of the diaphragm is indicative of a difference between the pressures of the two chambers. Such deformation/movement is detected by a device that has no physical contact with the diaphragm, for example, by an optical detector that detects a change in the shape of the diaphragm or a movement of a protrusion on the diaphragm.

7 Claims, 16 Drawing Sheets

(58) Field of Classification Search
CPC .......... G01L 19/0007; G01L 9/0042; G01L 19/0038; G01L 9/0073; G01L 9/0075; G01L 9/0054; G01L 9/0055; G01L 19/04; G01L 7/00; G01L 7/04; G01L 19/148; G01L 19/143; G01L 19/14; G01L 17/00; G01L 7/18; G01L 19/0092; G01L 15/00; G01L 9/0051; G01L 7/041; G01L 9/065; G01L 9/12; G01L 19/0618; G01L 9/0052; G01L 7/16; G01L 9/125; G01L 19/0609; G01L 9/007; G01L 19/003; G01L 9/0022; G01L 19/0627; G01L 19/0046; G01L 9/06; G01L 7/084; G01L 19/0636; G01L 13/02; G01L 19/0023; G01L 19/142; G01L 7/043; G01L 19/08; G01L 9/0002; G01L 19/02; G01L 9/008; G01L 19/141; G01L 9/006; G01L 11/02; G01L 23/10; G01L 23/18; G01L 19/0672; G01L 19/0681; G01L 9/0077; G01L 19/12; G01L 27/005; G01L 7/082; G01L 9/0044; G01L 19/0015; G01L 19/0069; G01L 7/063; G01L 9/0001; G01L 19/146; G01L 21/12; G01L 9/16; G01L 11/00; G01L 27/002; G01L 27/007; G01L 9/0026; G01L 19/00; G01L 9/0089; G01L 9/045; G01L 9/14; G01L 1/2281; G01L 11/025; G01L 11/008; G01L 19/0654; G01L 7/22; G01L 13/026; G01L 9/0047; G01L 9/0076; G01L 9/0025; G01L 13/00; G01L 9/0035; G01L 19/061; G01L 9/0005; G01L 9/10; G01L 9/0019; G01L 9/08; G01L 21/00; G01L 11/006; G01L 7/08; G01L 9/04; G01L 9/0041; G01L 9/0008; G01L 11/004; G01L 19/086; G01L 9/0057; G01L 1/18; G01L 19/083; G01L 19/069; G01L 19/10; G01L 19/16; G01L 13/023; G01L 7/048; G01L 9/0016; G01L 9/00; G01L 9/0027; G01L 9/0086; G01L 9/0079; G01L 9/0048; G01L 11/04; G01L 19/06; G01L 9/0091; G01L 1/20; G01L 11/002; G01L 23/24; G01L 7/182; G01L 19/0663; G01L 7/166; G01L 1/02; G01L 23/22; G01L 27/00; G01L 9/0036; G01L 9/0061; G01L 9/0039; G01L 23/125; G01L 9/0013; G01L 9/0092; G01L 21/04; G01L 7/104; G01L 9/0045; G01L 19/145; G01L 9/0033; G01L 1/142; G01L 9/0083; G01L 9/0098; G01L 7/24; G01L 1/2293; G01L 9/0029; G01L 9/02; G01L 21/22; G01L 9/0064; G01L 7/022; G01L 23/08; G01L 23/16; G01L 5/14; G01L 1/205; G01L 7/088; G01L 7/163; G01L 9/0007; G01L 23/222; G01L 1/2287; G01L 13/06; G01L 9/0085; G01L 1/16; G01L 1/2212; G01L 9/0004; G01L 21/14; G01L 23/02; G01L 9/003; G01L 9/025; G01L 9/085; G01L 1/14; G01L 1/148; G01L 9/0058; G01L 9/105; G01L 7/061; G01L 9/002; G01L 7/02; G01L 13/028; G01L 1/2231; G01L 23/28; G01L 9/0095; G01L 1/162; G01L 7/12; G01L 9/0032; G01L 9/0038; G01L 19/0076; G01L 7/024; G01L 21/10; G01L 1/246; G01L 19/149; G01L 7/086; G01L 1/005; G01L 7/06; G01L 7/102; G01L 1/2206; G01L 13/021; G01L 27/02; G01L 5/228; G01L 1/2262; G01L 1/24; G01L 1/26; G01L 23/00; G01L 9/0094; G01L 9/0082; G01L 1/125; G01L 11/06; G01L 9/0097; G01L 1/2268; G01L 19/144; G01L 21/30; G01L 21/34; G01L 23/221; G01L 7/187; G01L 7/20; G01L 23/26; G01L 7/068; G01L 1/225; G01L 23/32; G01L 7/14; G01L 1/144; G01L 1/165; G01L 23/12; G01L 1/146; G01L 1/241; G01L 7/045; G01L 1/086; G01L 13/04; G01L 7/108; G01L 9/18; G01L 1/22; G01L 17/005; G01L 5/18; G01L 1/127; G01L 1/245; G01L 21/32; G01L 1/183; G01L 1/2218; G01L 9/0023; G01L 1/243; G01L 23/145; G01L 5/0047; G01L 9/0088; G01L 1/106; G01L 5/0076; G01L 1/10; G01L 1/186; G01L 23/223; G01L 25/00; G01L 5/165; G01L 5/226; G01L 9/001; G01L 9/0017; G01L 1/044; G01L 3/245; G01L 1/08; G01L 21/16; G01L 3/1485; G01L 5/162; G01L 5/225; G01L 7/026; G01L 7/065; G01L 9/0014; G01L 1/04; G01L 1/242; G01L 21/24; G01L 3/10; G01L 5/0004; G01L 5/0052; G01L 9/005; G01L 1/00; G01L 1/103; G01L 1/2275; G01L 1/247; G01L 21/02; G01L 21/26; G01L 23/225; G01L 3/102; G01L 3/105; G01L 5/0038; G01L 5/223; G01L 5/24; G01L 7/028; G01L 7/10; G01L 9/0011; G01L 5/0028; G01L 5/243; G01L 1/083; G01L 1/12; G01L 21/36; G01L 23/04; G01L 23/14; G01L 23/30; G01L 3/103; G01L 5/00; G01L 5/102; G01L 5/133; G01L 5/166; G01L 7/185; G01L 1/255; G01L 21/08; G01L 5/0033; G01L 5/0057; G01L 5/161; G01L 5/22; G01L 1/042; G01L 1/122; G01L 1/2225; G01L 1/2243; G01L 1/2256; G01L 1/248; G01L 2009/0066; G01L 2009/0067; G01L 2009/0069; G01L 21/06; G01L 23/06; G01L 3/00; G01L 3/06; G01L 3/1478; G01L 3/1492; G01L 3/18; G01L 3/24; G01L 3/242; G01L 5/0061; G01L 5/08; G01L 5/10; G01L 5/101; G01L 5/108; G01L 5/16; G01L 5/1627; G01L 5/167; G01L 5/28; G01L 1/046; G01L 23/085; G01L 23/20; G01L 5/0071; G01L 5/008; G01L 5/06; G01L 5/171; G01L 7/106; A61M 1/3639; A61M 5/16854; A61M 1/3641; A61M 2205/3331; A61M 2205/12; A61M 2016/0027; A61M 2025/0002; A61M 16/044; A61M 27/006; A61M 2205/3344; A61M 2205/3306; A61M 2205/3355; A61M 2205/18; A61M 2205/3351; A61M 2205/583; A61M 1/16; A61M 2205/15; A61M 16/0078; A61M 5/142; A61M 16/0051; A61M 16/0084; A61M 2205/50; A61M 2205/581; A61M 5/007; A61M 5/1413; A61M 16/208; A61M 25/09; A61M 5/14232; A61M 1/732; A61M 1/74; A61M 2205/332; A61M 1/36224; A61M 16/021; A61M 16/0858; A61M 2005/16868; A61M 2205/0244; A61M 2205/70; A61M 2205/702; A61M 2205/8206; A61M
5/14276; A61M 16/00; A61M 2205/3317;
A61M 1/3621; A61M 1/3643; A61M
2005/16872; A61M 2205/128; A61M
2205/14; A61M 39/22; A61M 5/145;
A61M 1/3644; A61M 2016/0021; A61M
2025/09083; A61M 2202/0482; A61M
2205/16; A61M 2205/7536; A61M
25/10182; A61M 5/16827; A61M
5/16831; A61M 5/16859; A61M 1/36225;
A61M 1/36226; A61M 1/3627; A61M
16/0409; A61M 16/0677; A61M
2016/0024; A61M 2205/3375; A61M
5/141; A61M 5/14228; A61M 5/14244;
A61M 5/158; A61M 1/3403; A61M
1/3607; A61M 1/3622; A61M 1/61;
A61M 16/0434; A61M 16/08; A61M
16/0816; A61M 2005/16863; A61M
2025/0166; A61M 2202/0208; A61M
2205/276; A61M 2205/3348; A61M
2205/3368; A61M 2205/7527; A61M
25/10185; A61M 25/10187; A61M
5/14546; A61M 1/1692; A61M 1/3609;
A61M 1/362261; A61M 15/00; A61M
16/20; A61M 16/209; A61M 2005/14252;
A61M 2205/0294; A61M 2205/122;
A61M 2205/3334; A61M 2205/3358;
A61M 2205/3569; A61M 2205/502;
A61M 2205/587; A61M 2207/00; A61M
2209/02; A61M 3/0216; A61M 39/08;
A61M 5/14248; A61M 5/152; A61M
5/168; A61M 5/16877; A61M 5/365;
A61M 1/154; A61M 1/30; A61M 1/3653;
A61M 1/3659; A61M 1/77; A61M
16/0003; A61M 16/0057; A61M 16/06;
A61M 16/104; A61M 2005/14264; A61M
2016/0036; A61M 2205/273; A61M
2205/33; A61M 2205/3313; A61M
2205/3337; A61M 2205/3365; A61M
2205/3386; A61M 2205/75; A61M
2205/7518; A61M 2230/30; A61M 25/00;
A61M 25/005; A61M 25/007; A61M
25/10184; A61M 39/00; A61M 39/10;
A61M 5/14224; A61M 5/14526; A61M
5/1456; A61M 5/14566; A61M 5/16886;
A61M 5/486; A61M 5/5086; A61M
60/531; A61M 1/155; A61M 1/28; A61M
1/281; A61M 1/284; A61M 1/288; A61M
1/302; A61M 1/303; A61M 1/306; A61M
1/34; A61M 1/341; A61M 1/36222;
A61M 1/362264; A61M 1/362265; A61M
1/362266; A61M 1/3652; A61M 1/3655;
A61M 1/367; A61M 1/66; A61M 1/73;
A61M 1/90; A61M 1/96; A61M 1/982;
A61M 16/024; A61M 16/0875; A61M
16/12; A61M 2005/1405; A61M
2025/09175; A61M 2205/3382; A61M
2205/3523; A61M 2205/582; A61M
2206/20; A61M 25/1018; A61M 3/0201;
A61M 3/022; A61M 5/14; A61M 5/1454;
A61M 5/16881; A61M 60/178; A61M
60/216; A61M 1/08; A61M 1/14; A61M
1/1522; A61M 1/1524; A61M 1/1561;
A61M 1/1565; A61M 1/159; A61M
1/1601; A61M 1/1605; A61M 1/1617;
A61M 1/301; A61M 1/308; A61M
1/3472; A61M 1/362227; A61M
1/362262; A61M 1/3626; A61M 1/3656;
A61M 1/3661; A61M 1/3693; A61M
1/3696; A61M 1/72; A61M 1/80; A61M
11/00; A61M 11/042; A61M 13/003;
A61M 15/0083; A61M 15/06; A61M
16/0009; A61M 16/0072; A61M 16/04;
A61M 16/0447; A61M 16/0683; A61M
16/0833; A61M 16/0866; A61M 16/0883;
A61M 16/1045; A61M 16/14; A61M
16/16; A61M 16/206; A61M 2005/14268;
A61M 2005/14513; A61M 2005/14553;
A61M 2005/2411; A61M 2016/0042;
A61M 2016/102; A61M 2025/0037;
A61M 2025/0213; A61M 2025/0246;
A61M 2025/09008; A61M 2025/09141;
A61M 2025/1022; A61M 2039/229;
A61M 2205/0227; A61M 2205/0233;
A61M 2205/051; A61M 2205/073; A61M
2205/125; A61M 2205/17; A61M
2205/21; A61M 2205/3327; A61M
2205/3341; A61M 2205/3379; A61M
2205/3592; A61M 2205/584; A61M
2205/585; A61M 2209/045; A61M
2210/0612; A61M 2210/101; A61M
2210/125; A61M 2230/207; A61M
2230/40; A61M 2230/42; A61M 2240/00;
A61M 25/0082; A61M 25/02; A61M
25/04; A61M 25/0662; A61M 25/10;
A61M 25/10181; A61M 25/10188; A61M
25/104; A61M 29/02; A61M 3/0208;
A61M 3/0212; A61M 3/0233; A61M
3/0258; A61M 3/0283; A61M 39/0208;
A61M 39/223; A61M 39/24; A61M
39/28; A61M 5/00; A61M 5/002; A61M
5/1408; A61M 5/1418; A61M 5/14212;
A61M 5/14216; A61M 5/1452; A61M
5/1458; A61M 5/1483; A61M 5/1684;
A61M 5/172; A61M 5/1723; A61M 5/24;
A61M 5/315; A61M 5/31511; A61M
5/36; A61M 5/427; A61M 5/48; A61M
60/148; A61M 60/554; A61M 1/152;
A61M 1/36223; A61M 1/362263; A61M
1/3623; A61M 1/742; A61M 1/743;
A61M 1/772; A61M 1/774; A61M 1/78;
A61M 1/782; A61M 1/804; A61M 1/81;
A61M 1/85; A61M 1/91; A61M 16/0081;
A61M 16/022; A61M 16/0488; A61M
16/049; A61M 16/0841; A61M 16/107;
A61M 16/202; A61M 2202/02; A61M
2205/13; A61M 2205/3324; A61M
2205/3372; A61M 2205/3576; A61M
25/0069; A61M 3/0202; A61M 39/227;
A61M 5/16836; A61M 60/113; A61M
60/135; A61M 60/143; A61M 60/205;
A61M 60/232; A61M 60/295; A61M
60/32; A61M 60/37; A61M 60/422;
A61M 60/497; A61M 60/538; A61M
60/546; A61M 60/585; A61M 60/849;
A61M 60/857

USPC .................................................. 73/700–756
See application file for complete search history.

(56) References Cited

U.S. PATENT DOCUMENTS

| | | | |
|---|---|---|---|
| 5,052,807 | A | 10/1991 | Juday |
| 5,693,008 | A | 12/1997 | Brugger et al. |
| 5,983,727 | A * | 11/1999 | Wellman ............... G01L 9/0072 73/705 |
| 7,721,843 | B1 | 5/2010 | Belenger et al. |
| 8,092,414 | B2 | 1/2012 | Schnell et al. |
| 8,960,010 | B1 | 2/2015 | Crnkovich et al. |
| 10,422,712 | B2 | 9/2019 | Abo et al. |
| 10,481,028 | B2 | 11/2019 | Imai et al. |
| 2002/0100316 | A1 | 8/2002 | James et al. |
| 2004/0261534 | A1 | 12/2004 | Boukhny et al. |
| 2007/0179422 | A1 | 8/2007 | Schnell et al. |
| 2009/0171224 | A1 | 7/2009 | Jochim et al. |
| 2014/0012120 | A1 | 1/2014 | Cohen et al. |
| 2017/0028119 | A1 | 2/2017 | Brugger et al. |

OTHER PUBLICATIONS

International Search Report and Written Opinion issued in PCT/US2020/22341, dated Jul. 17, 2020.

Invitation to Pay Additional Fees dated May 7, 2020 for International Patent Application No. PCT/US2020/022341.

* cited by examiner

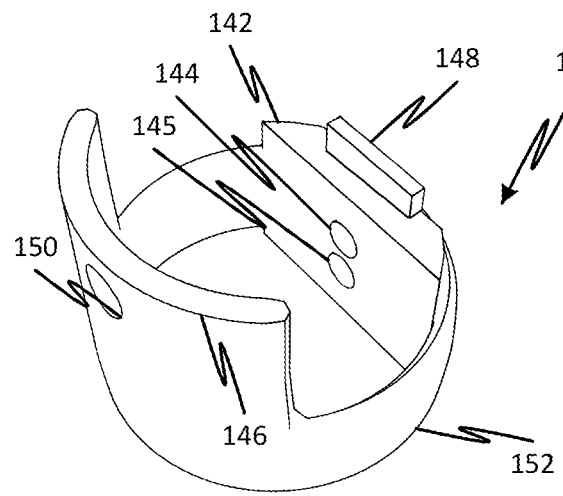
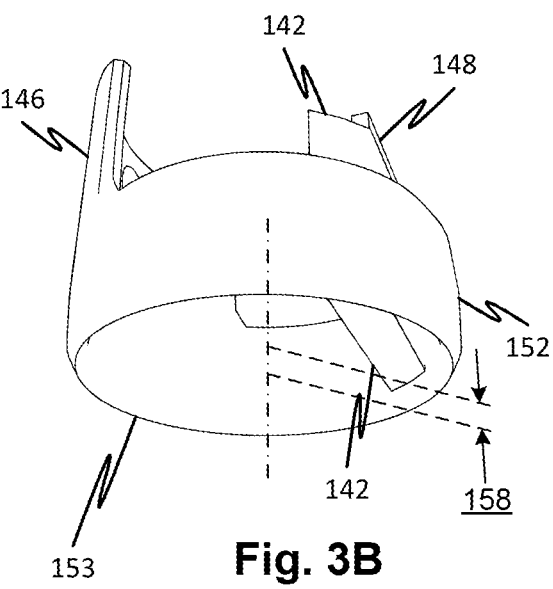
Fig. 3A
Fig. 3B
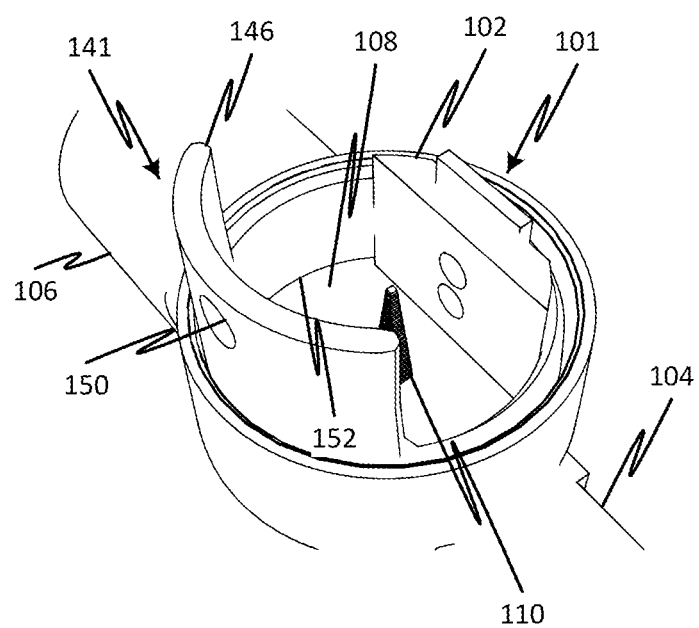
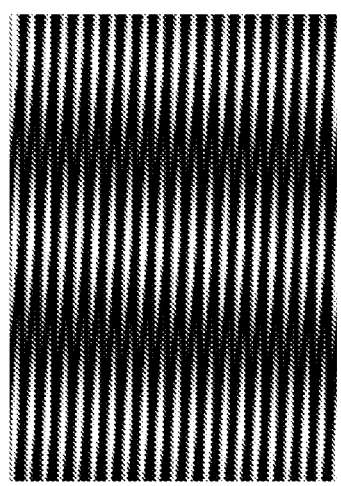
Fig. 3C
Fig. 3D

OPTICAL PRESSURE MEASUREMENT DEVICES, METHODS, AND SYSTEMS

CROSS-REFERENCE TO RELATED APPLICATIONS

This Application is a U.S. national stage filing under 35 U.S.C. § 371 of International Application No. PCT/US2020/022341, filed Mar. 12, 2020, which claims priority to and the benefit of U.S. Provisional Patent Application No. 62/818,962 filed Mar. 15, 2019, each of which are hereby incorporated by reference in their entireties.

FIELD

The disclosed subject matter relates generally to pressure measurement devices, methods, and systems, and more particularly, to pressure measurement devices, methods, and systems that use an optical pressure measurement pod.

BACKGROUND

Pressure transducers are used widely for pressure measurement. An example prior art device is described in U.S. Pat. No. 4,576,181 and illustrated in FIG. 1A. Such devices require connection to a flow channel or chamber to provide fluid communication with a sensor portion. For example, a flow channel 1332 of a prior art device provides fluid communication between a diaphragm 45 and a vessel or conduit 330 containing a fluid whose pressure is to be measured, from some flow or containment system 47. An intermediate fluid in a space 35 on an opposite side of the diaphragm 45 communicates with a pressure transducer 40. The fluid whose pressure is to be measured exerts a pressure on the diaphragm 45 in turn exerting a pressure on the intermediate fluid in space 35. A pressure transducer 40 generates a signal corresponding to the pressure of the intermediate fluid in the space 35 by any of various mechanisms, typically involving a strain gage or load cell. Another example of this type of device is described in U.S. Pat. No. 8,092,414 which is often identified as a pressure pod because of its general shape. Another known device for measuring pressure is illustrated in FIG. 1B. In this device, a thin plate 30 has a strain gauge 10 on a back surface 31 thereof. A pliant thin-walled vessel 20 rests against a front surface 32 of the thin plate 30. When fluid 25 inside the vessel 20 pressurizes the vessel, which is bounded by walls 15 and 22, thin plate 30 flexes, stretching the strain gauge 10 attached to it, thereby causing a signal from which pressure can be correlated by calibration.

The pressure sensor of FIG. 1B may be employed in medical systems and devices that transport biological fluids. In such systems, the use of certain plastics is very common, due to its durability, flexibility, low cost, and low chemical and biological reactivity. Such plastics, however, when strained, are susceptible to change in terms of their elastic response. For example, if substantially deformed, plastic vessels such as 20 in FIG. 1B will exhibit a condition known as "creep", causing the displacement-versus-pressure response to change over time. Creep is caused by changes in the conformation of polymer molecules over time. Creep may lead to errors in measurement of pressure changes in a configuration such as that of FIG. 1B. A plastic diaphragm of the form of diaphragm 45 will also exhibit creep.

Referring to FIG. 1C, another type of prior art pressure sensor is shown in which a pressure transducer 50 is in pressure communication with an interior 70 of a drip chamber 60. Blood flows through an inlet tube 65 and out an outlet tube 75 while a trapped volume of air 62 communicates pressure to the pressure transducer 50 through a coupling tube 57. An isolator 55 protects the pressure transducer 50 by preventing any flow through it via a flexible membrane within it (not shown).

SUMMARY

Embodiments provide a pressure pod that includes two chambers separated by a diaphragm where a deformation/movement of the diaphragm is indicative of a difference between the pressures of the two chambers. Such deformation/movement is detected by a device that has no physical contact with the diaphragm, for example, by an optical detector that detects a change in the shape of the diaphragm or a movement of a protrusion on the diaphragm. In some embodiment, the pressure pod is medically sealed, disposable, and inexpensive.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 3A and 3B show respective views of an optical transducer configured for engagement with the pressure pod of FIG. 2A according to the disclosed embodiments.

FIG. 3C shows the optical transducer of FIGS. 3A and 3B when engaged to the pressure pod of FIG. 2A according to the disclosed embodiments.

FIG. 3D shows the appearance of a filtered pattern detected by the optical transducer of FIGS. 3A and 3B according to the disclosed embodiments.

DETAILED DESCRIPTION

Figure 1A:
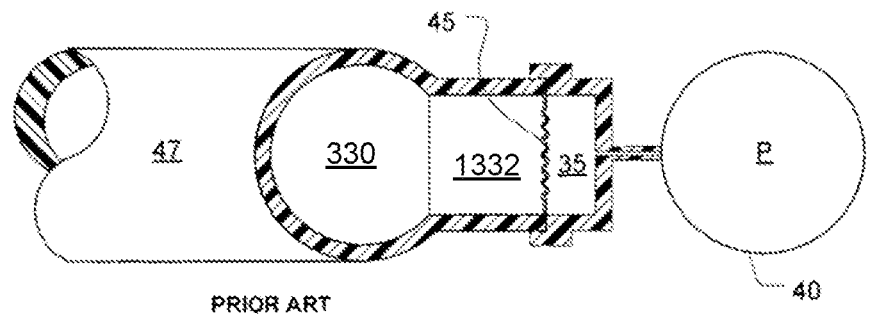
FIGS. 1A-1C show pressure measurement devices according to the prior art.
Figure 1B:
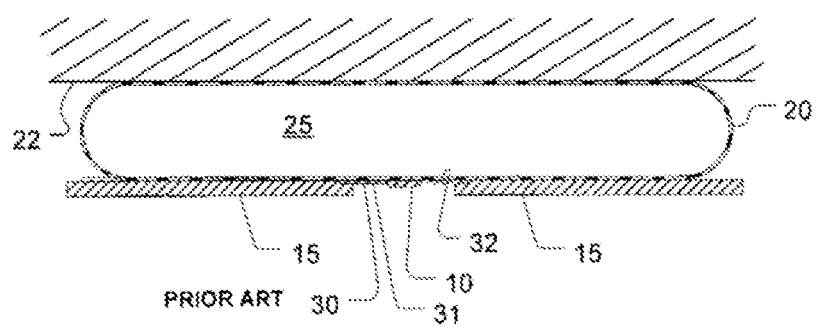
Figure 1C:
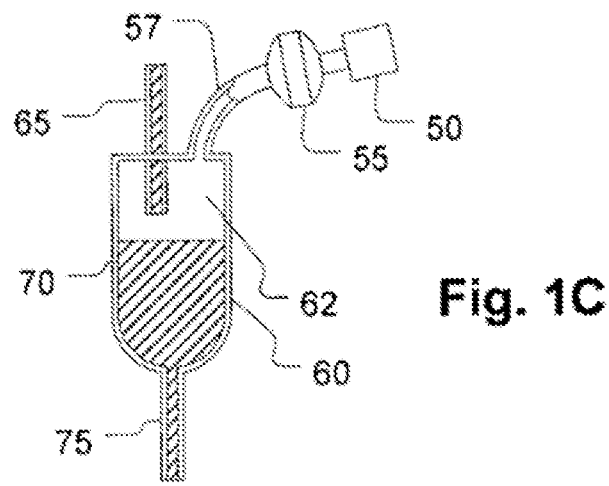
Figure 2A:
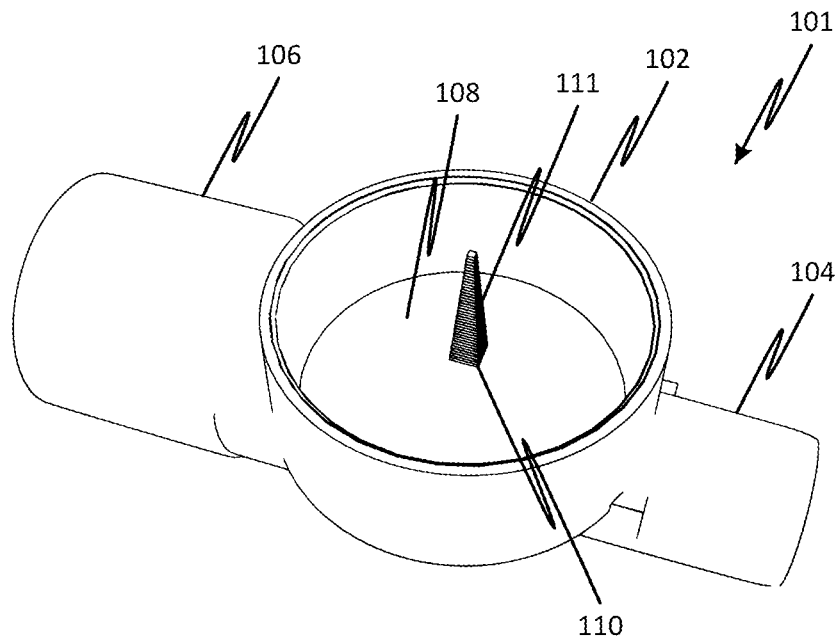
FIGS. 2A and 2B show pressure pods according to the disclosed embodiments.

FIG. 2A shows a pressure pod 101 according to the disclosed embodiments. The pressure pod 101 has a first port 106 and a second port 104. In the present embodiment, the first port 106 is larger to accommodate a larger tube in an embodiment where the pressure pod 101 is to be directly connected to a pump tube portion. The second port 104 is for connection to a smaller diameter tube. A diaphragm 108 seals a portion of a continuous lumen spanning between 106 and 104 with a cross-sectional area that is substantially uniform to reduce the risk of dead zones that can cause clotting/coagulation when the pressure measurement device is used for measuring blood pressure. Alternatively, the cross section may vary as a result of the positive draft angles used to allow the mold pins to be removed so that there is a narrowing from one port toward the center of the pod and then a widening of the cross section on the way to the opening of the other port. It is possible for the pins to be shaped such that the flow area is largest in the middle despite the positive draft angles, but certain benefits accrue where the area changes little, including the reduction in turbulence otherwise caused by flow deceleration. Note that flow area inserts may be used to adapt tubes to the ports so that the requirements of the beneficial molding process described herein do not have to constrain choices for connecting tubes to the pod.

The pressure in the lumen causes movement/deformation of the diaphragm 108, which in turn causes a movement of an indicator 110 configured as a protrusion on the diaphragm 108. The surface of the indicator 110 is embossed or imprinted by markings 111 so that the movement of the indicator 110 can be optically monitored by a measurement device (not shown) that engages a recess rim 102 of the pressure pod 101. The engagement is suitable for immobilizing the support of the diaphragm 108 and helping to ensure accurate measurement.

Figure 2B:
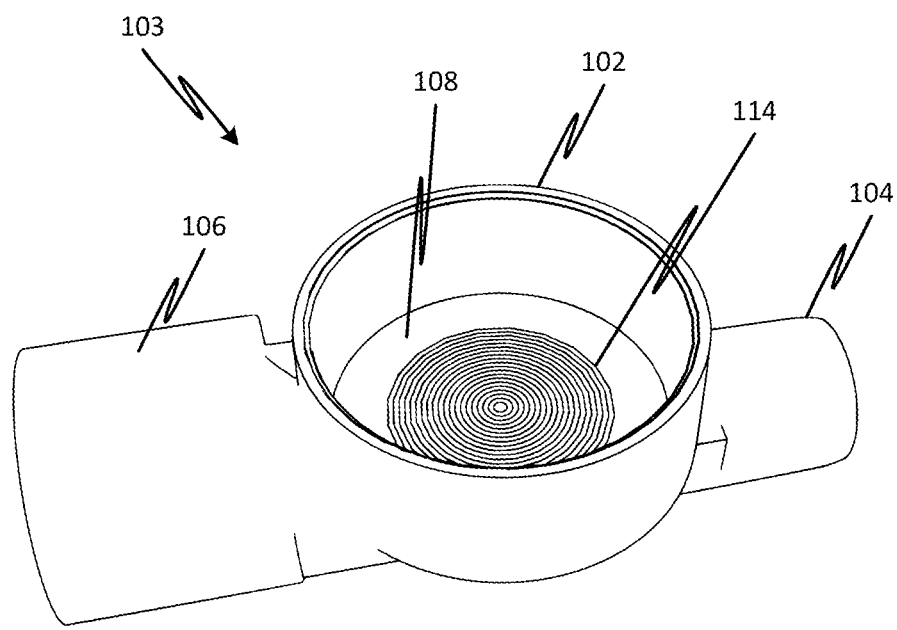

FIG. 2B shows another pressure pod 103 according to the disclosed embodiments. The pressure pod 103 is the same as the pressure pod 101 except that it does not include the indicator 110. Instead, movement/deformation of the diaphragm 108 is detected by optically monitoring embossed or imprinted markings 114 on the surface of the diaphragm 108. Other alternative embodiments may optically monitor markings on both a diaphragm and an indicator configured as a protrusion on the diaphragm.

In one embodiment, the markings on the diaphragm 108 and/or the indicator 110 may be painted thereon after the pressure pod has been molded. In one embodiment, the markings on the diaphragm 108 and/or the indicator 110 are etched by a laser. In one embodiment, the markings on the diaphragm 108 and/or the indicator 110 may be glued/attached thereon. In further embodiments, the markings may be printed on the diaphragm 108 and/or the indicator 110 such as by means of silk-screening or inkjet. In still other embodiments, the markings on the diaphragm 108 and/or the indicator 110 may be molded into the diaphragm 108 or the indicator 110. Note that for molding, the markings may have a neutral or positive draft to permit easy separation from the mold. For example, a staircase may be formed on a pyramidal indicator. The staircase may be made to stand out by illuminating to create shadows on each step.

FIGS. 3A and 3B show respective views of an optical transducer 141 configured for engagement with the pressure pod 101 of FIG. 2A, and FIG. 3C shows the optical transducer of FIGS. 3A and 3B when assembled on the pressure pod 101 of FIG. 2A, according to the disclosed embodiments. The optical transducer 141 has a support insert 152 that is configured to fit within the recess rim 102 of the pressure pod 101 to locate it precisely relative to a supporting transducer element.

The support insert 152 supports a camera/light source body 142 and an arm 146. The arm 146 includes an opening for fastener 150 so that the optical transducer 141 may be fastened to another assembly in a system. The camera/light source 142 includes a light source 145, a camera 144, and a connector 148 for camera 144. When the support insert 152 is fitted within the recess rim 102 of the pressure pod 101, the light source 145 can reflect light on the indicator 110 so that the camera 144 can take images of the indicator 110 when controlled by a controller via the connector for camera 148.

The body of the camera/light source 142 may be spaced apart (as indicated at 158) from the rim 153 of the support insert 152 so as not to interfere with displacement of the diaphragm 108.

In some embodiments, the camera 144 may include a Moire filter. Generally, a Moire filter is a filter with alternating transparent and opaque (non-light-transmitting) portions forming, for example, concentric circles, a grid, parallel lines, etc. When the markings on the indicator 110 have a same or similar pattern as the Moire filter and are misaligned with respect to the Moire filter, a Moire pattern may be observed in the images of the markings obtained by the camera 144 through the Moire filter. Generally, a Moire pattern is formed by placing two templates of alternating transparent and opaque areas against each other. When the template patterns are misaligned from a certain point of view, the superposition and interference of the template patterns appears from that point of view as alternating light and dark zones that are larger/coarser than the original template patterns, and the misalignment causes the resulting pattern to appear to run. The resulting pattern is indicative of a beat frequency of the interference of the template patterns which is lowers than the frequency of the alternating patterns in the templates. Using the resulting pattern, a relative position may be determined, for example, as disclosed in U.S. Pat. No. 5,052,807.

In one embodiment, at least two cameras with respective Moire filters are configured to obtain respective Moire patterns by taking images of the indicator 110. In these embodiments, the Moire patterns may be used in combination for determining a movement of the indicator 110 and/or calibrating the pressure measurement device.

FIG. 3D shows the appearance of a filtered pattern detected by the optical transducer 141 when the camera 144 includes a Moire filter with a pattern of parallel lines and is misaligned with parallel line markings on the indicator 110. In one embodiment, a pre-determined function may be used to relate a change in the Moire pattern detected by the camera 144 with a movement of the indicator 110. The pre-determined function may be compiled by training a controller of the optical transducer 141 with known movements of the indicator 110 and the resulting Moire patterns obtained by the camera 144.

Figure 4A:
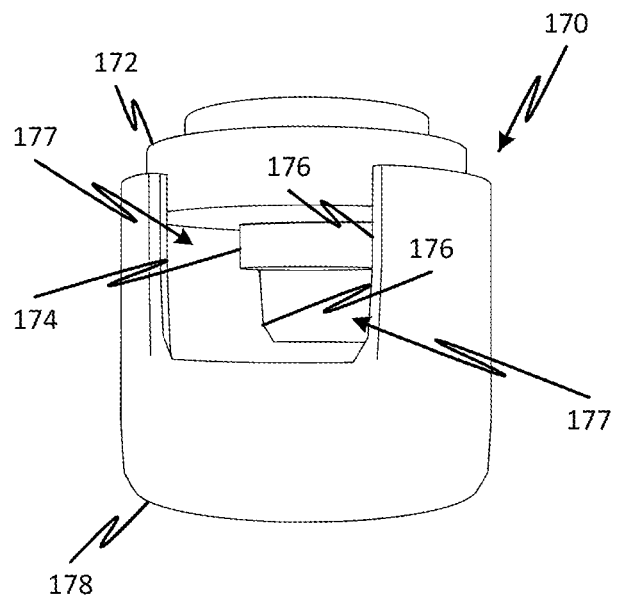
FIG. 4A shows an optical transducer configured for engagement with the pressure pod of FIG. 2B according to the disclosed embodiments.
Figure 4B:
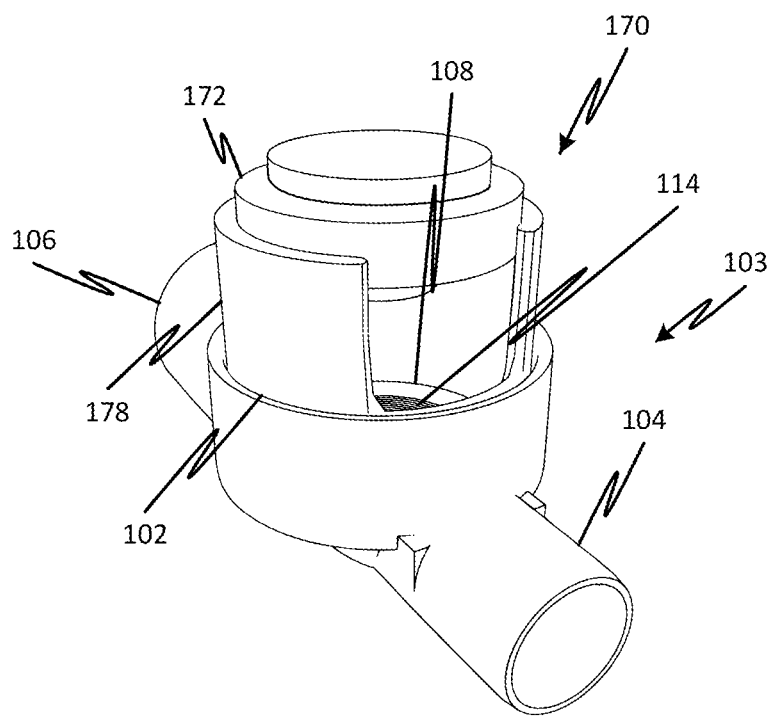
FIG. 4B shows the optical transducer of FIG. 4A when assembled on the pressure pod of FIG. 2B according to the disclosed embodiments.

FIG. 4A shows an optical transducer 170 configured for engagement with the pressure pod 103 of FIG. 2B and FIG. 4B shows the optical transducer 170 of FIG. 4A when assembled on the pressure pod 103 of FIG. 2B according to the disclosed embodiments. Optical transducer 170 includes a support insert 178 that is configured to fit within the recess rim 102 of the pressure pod 103.

The support insert 178 supports, between two pillars 176, a camera 172 with a camera lens 174 facing the diaphragm 108 of the pressure pod 103 so that the camera 172 can take images of the diaphragm 108 when controlled by a controller. The pillars define notches 177 that may allow for the use of a light source outside the support insert 178. Alternatively, the body of the camera 172 may have an integrated light source. An outside light source may provide better for shadowing molded-in ridges to form the indicator.

Figure 4C:
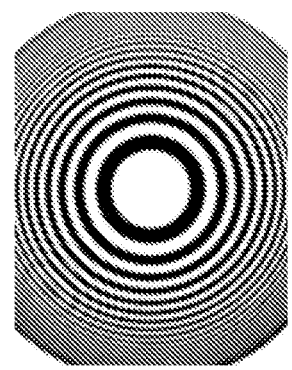
FIG. 4C shows the appearance of a filtered pattern detected by the optical transducer of FIG. 4A according to the disclosed embodiments.

In embodiments, the camera lens 174 includes a Moire filter including alternating transparent and opaque portions forming, for example, concentric circles, a grid, parallel lines, etc. When the markings on the diaphragm 108 have a same or similar pattern as the Moire filter and are misaligned with respect to the Moire filter, a Moire pattern may be observed in the images of the markings obtained by the camera 172 through the Moire filter of the camera lens 174. FIG. 4C shows the appearance of a filtered pattern detected by the optical transducer 170 when the lens 174 includes a Moire filter with a pattern of concentric circles and is misaligned with same or similar concentric circle markings on the diaphragm 108.

In embodiments, the movement/deformation of the diaphragm may be detected by using the disclosed Moire patterns in super-resolution imaging. Super-resolution imaging refers to improving the resolution of images obtained by an imaging system. In one embodiment, when the resolution of the markings on a marker or diaphragm is beyond the diffraction limit, a Moire filter that is coarser (lower-resolution) than the markers may be used to obtain images from which the high-resolution markings can be inferred. Accordingly, more accurate pressure measurement may be accomplished.

One embodiment provides a pressure measurement device that determines a pressure based on Moire patterns resulting from taking images of markings on a diaphragm of a pressure pod as well as markings on an indicator on the diaphragm. The Moire patterns may be obtained by respective cameras including respective filters to obtain images of the diaphragm and images of the protrusion on the diaphragm.

Figure 4D:
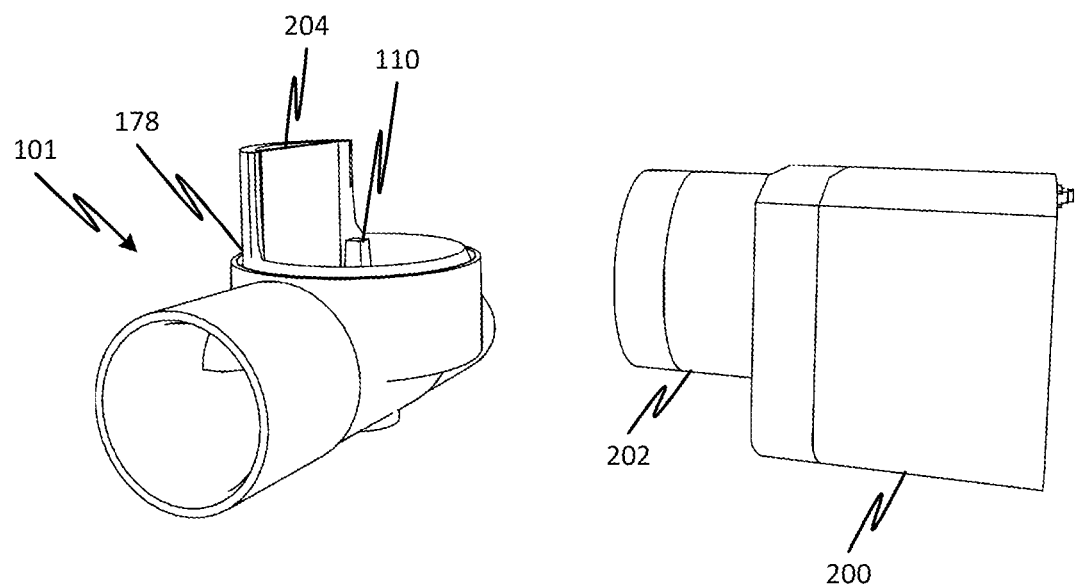
FIGS. 4D and 4E show an alternative pressure measurement device that includes the pressure pod of FIG. 2A according to the disclosed embodiments.
Figure 4E:
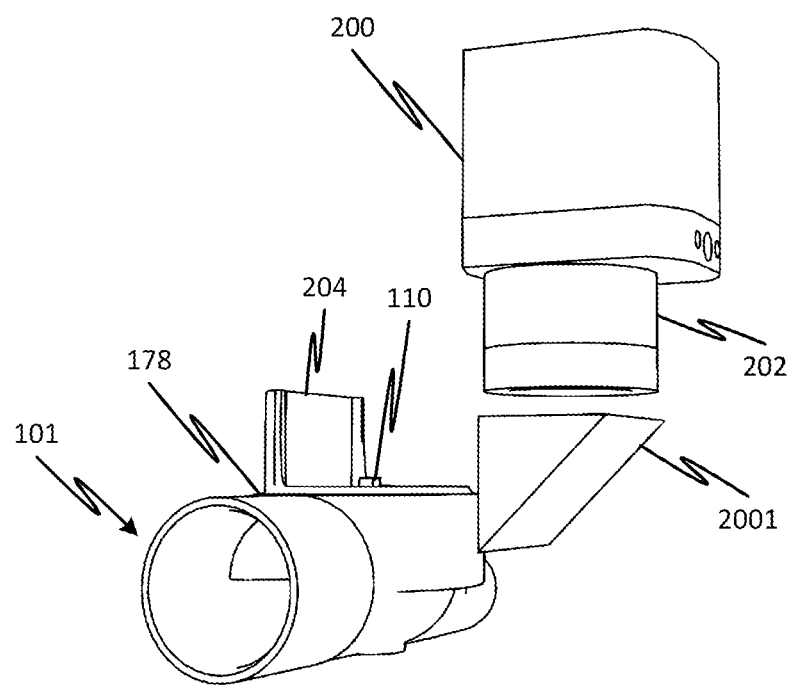

FIGS. 4D and 4E show an alternative pressure measurement device that includes the pressure pod 101 of FIG. 2A and a camera 200 for monitoring movements of the indicator 110. A support insert 178 is configured to fit within the recess rim 102 of the pressure pod 101 and includes a background screen 204 against which images of the indicator 110 can be taken. A camera lens 202 of the camera 200 may be oriented to face the background screen 204 as shown in FIG. 4D. Alternatively, the camera lens 202 may be oriented to be in parallel with the background screen 204 as shown in FIG. 4E, and a beam director 2001 may be configured to direct a beam from the indicator 110 to the camera 200 so that the camera 200 may take images of the indicator 110 against the background screen 204.

One embodiment provides functionality to prevent and/or account for any "creep" in the diaphragm 108. Creep, or plastic deformation, occurs when the diaphragm 108 gradually generates a lower elastic rebound after being deformed over time. This produces hysteresis in the pressure signal. As a result of creep, the pressure signal from a calibration becomes less related to the pressure signal after calibration. In embodiments, a negative pressure is periodically introduced to exercise the diaphragm 108 (for example, for 1% of the duty cycle) to avoid creep. In other embodiments, control check algorithms are used to determine if creep occurs. One embodiment minimizes diaphragm deformation in configurations in which the material of which the diaphragm is made is prone to creep. This translate to a reduced susceptibility of the apparatus to respond variably over time to pressure in the pressure pod due to the creep, and to a smoother monotonic relationship between pressure and diaphragm deformation/movement. The problems relating to creep may also be overcome by suitable choice of material. For example, a material which is not subject to creep may be used for the diaphragm 108. Alternatively, or in combination with such a material selection, the wall thickness of the diaphragm may be reduced.

In embodiments, the material and/or thickness of the diaphragm 108 is selected to further account for hoop strength in pressure measurement. Hoop strength refers to the stress produced by the pressure of the fluid in a pipe and applied circumferentially to the pipe wall in a plan perpendicular to the pipe's longitudinal axis. A vessel or tube with a substantially circular or elliptical cross-section has significant hoop strength requiring a great deal of material strain to displace a diaphragm embedded thereon such as the diaphragm 108. In addition, the thickness of the diaphragm 108 affects the degree of strain to which the material of the tube or vessel must be subjected to generate a displacement/deformation of the diaphragm 108. In embodiments, the diaphragm 108 may be formed of a flexible polymer.

Figure 5A:
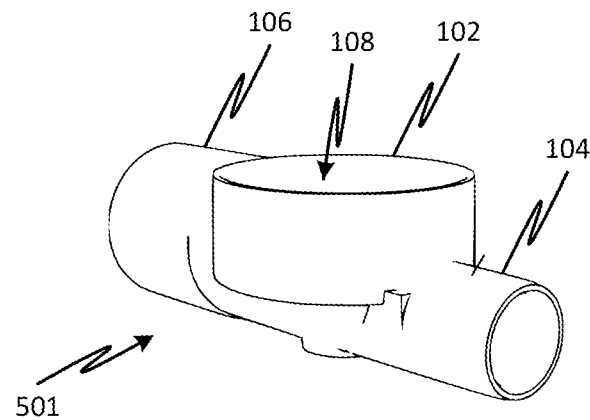
FIGS. 5A and 5B show a pressure pod having a straight channel configuration according to embodiments of the disclosed subject matter.
Figure 5B:
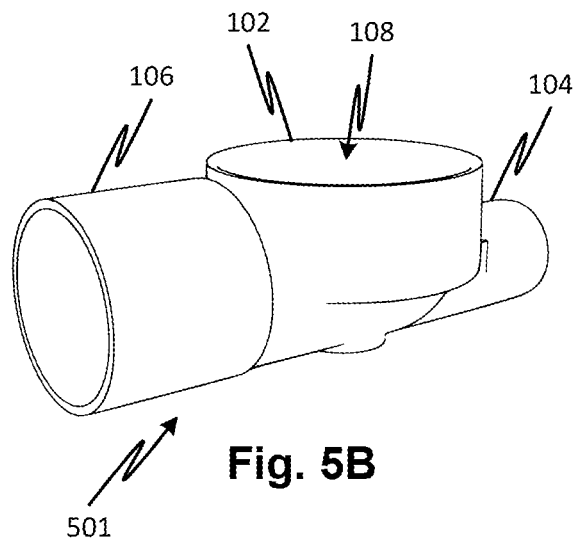
Figure 5C:
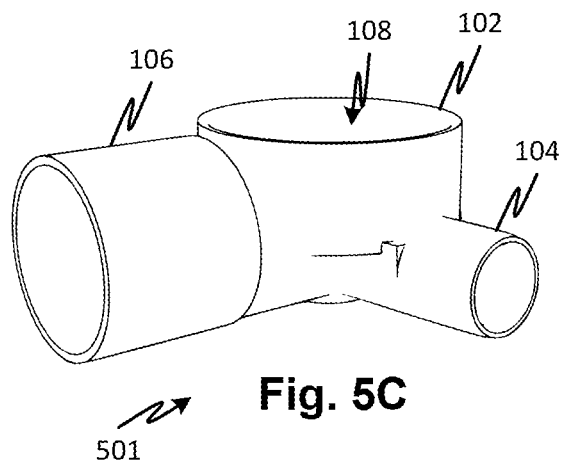
FIGS. 5C and 5D show pressure pods having a right angle channel in left and right hand configurations respectively, according to embodiments of the disclosed subject matter.
Figure 5D:
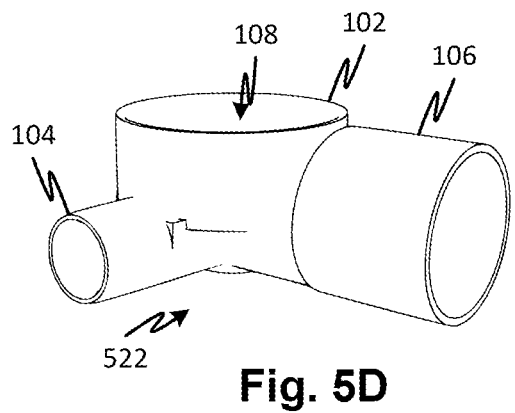
Figure 6A:
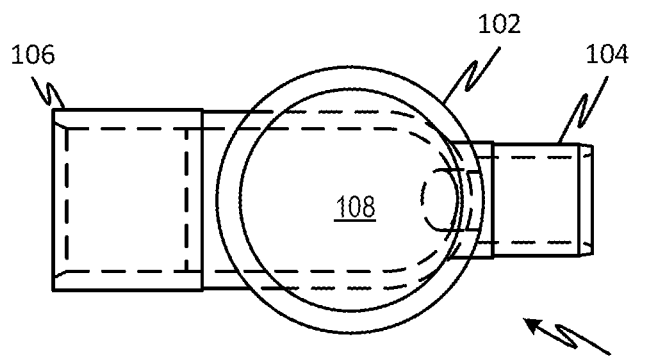
FIGS. 6A through 6C show respective embodiments of pressure pods having configurations with channels that proceed at various angles according to respective embodiments of the disclosed subject matter.
Figure 6B:
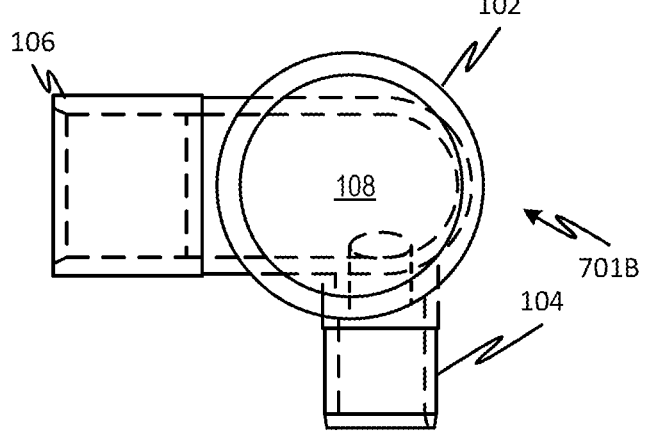
Figure 6C:
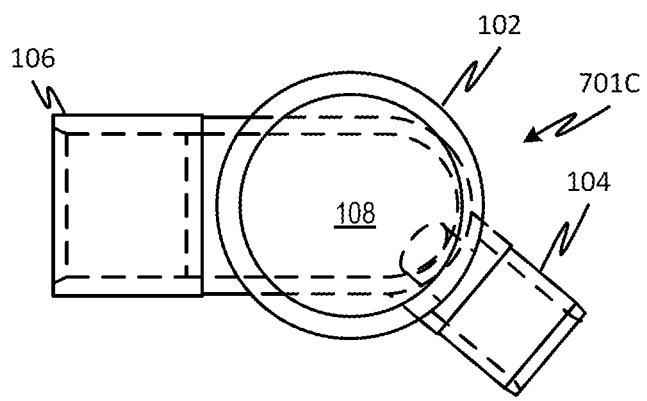

FIGS. 5A and 5B show a pressure pod with a straight fluid channel with ports 104 and 106, a diaphragm 108, and a recess rim 102 as described with regard to other embodiments and similar to one described in International Patent Publication WO2012166980 ('980). FIGS. 5C and 5D show left hand and right hand 90 degree turn pods with channels shaped to bend at right angles. As may be confirmed by inspection of FIGS. 6A through 6C, the pods of FIGS. 5A and 5B may be molded with an integral diaphragm in the manner described in '980. FIG. 6C shows a pod 701C with a fluid channel that turns at an angle between 0 and 90 degrees. It can be seen that injection molding pins may be used to form the inlet and outlet channels as well as the pressure measurement chamber in the fluid channel below and adjacent the diaphragm 108. Also, it will be observed that the diaphragm may be formed in the molding of the entire pressure pod of any of the embodiments shown at 701A-701C.

Figure 6D:
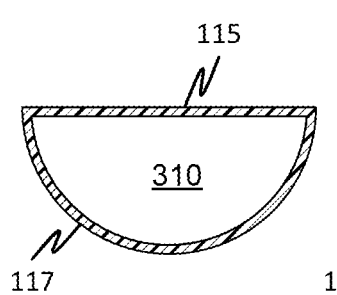
FIGS. 6D through 6H and 6J show cross-section views through embodiments of pressure pods under various pressure conditions.
Figure 6E:
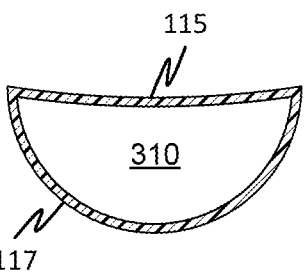
Figure 6F:
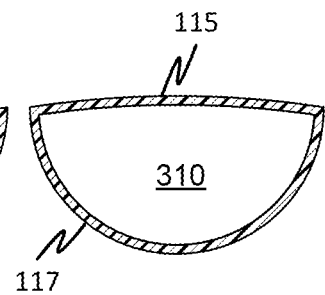
Figure 6G:
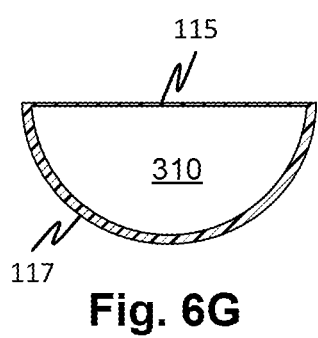
Figure 6H:
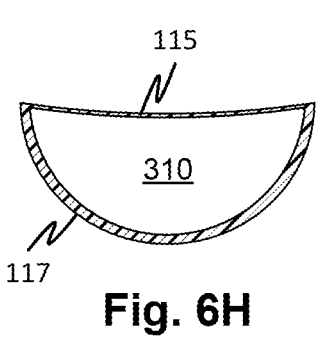
Figure 6J:
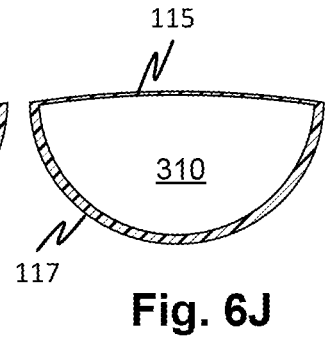
Figure 6K:
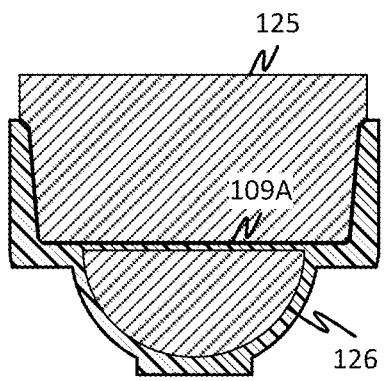
FIGS. 6K and 6L show a molding operation according to embodiments of the disclosed subject matter.
Figure 6L:
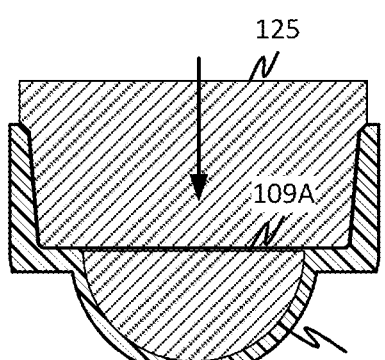

FIG. 6D shows a cross-section of a pod portion having a channel 310 defined by a channel wall 117 and a diaphragm 115 integrally formed with the channel wall 117 for example by injection molding. When there is a negative pressure in the channel, the diaphragm 115 flexes and is pulled inwardly toward the channel as shown in FIG. 6E. When there is a positive pressure in the channel 310, the diaphragm 115 flexes and is pushed outwardly as shown in FIG. 6F. The flexion of the diaphragm 115 is attended by strain of the material due to the finite thickness of the diaphragm 115. This strain can be reduced for a given degree of flexion by making the diaphragm 115 thinner as shown in FIGS. 6G through 6J. By reducing the strain, the magnitude of creep can be reduced. FIG. 6K shows a molding operation for a pressure pod 501 shown in cross-section. A pin 125 forms an integral diaphragm 109A in cooperation with a pin 126 by molding. Other parts of the mold are not shown. To make the diaphragm thin, an operation known as coining may be employed by, after flowing molten plastic through the mold passage corresponding to the diaphragm 109A, forcing the pin 125 downwardly to reduce the volume of this mold passage and press the still softened plastic out of the mold passage as shown in FIG. 6L.

Figure 7A:
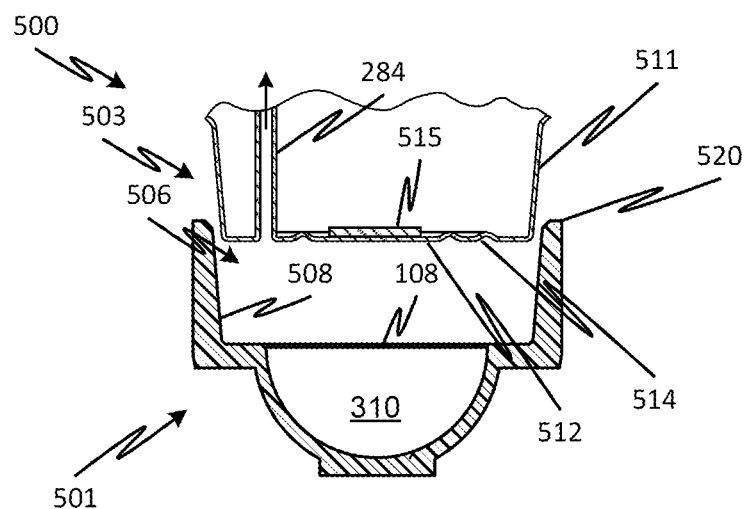
FIGS. 7A and 7B show a transducer that attaches to a pressure pod by means of a vacuum attachment system with FIG. 7A showing the pod ready for engagement with the transducer and FIG. 7B showing the pressure pod in engagement with the transducer, according to embodiments of the disclosed subject matter.
Figure 7B:
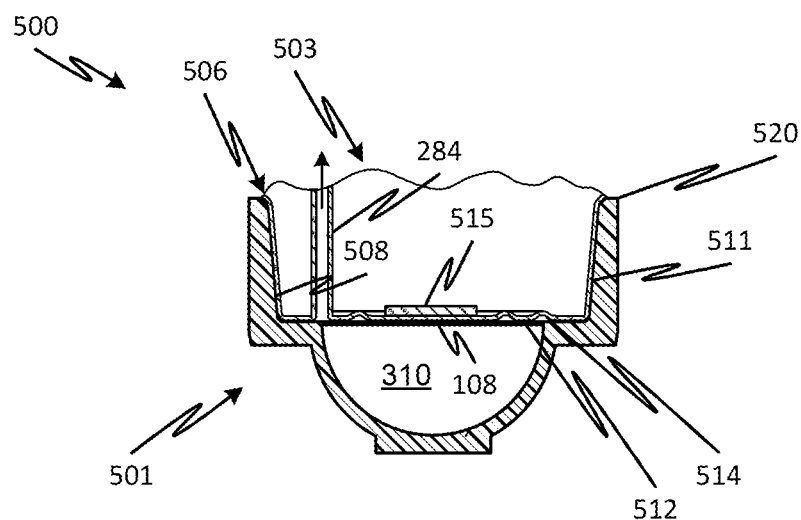

FIGS. 7A and 7B show a pressure sensor 500 that includes a pressure pod 501 and a transducer 503. The transducer 503 has a cylindrical housing 511 that attaches to the pressure pod 501 by means of a vacuum attachment system with FIG. 7A showing the pod 501 ready for engagement with the transducer 503 and FIG. 7B showing the pressure pod 501 engaged with the transducer 503. The vacuum attachment system draws air through a vacuum line 284 to generate a vacuum between the pod 501 diaphragm 108 and a force input plate 512. The force input plate 515 has a strain gauge 515 that converts displacement of the diaphragm 108 into a pressure indication of fluid pressure in the channel 310 of the pressure pod 501. As a result of the vacuum, the force input plate 512 follows the diaphragm when a positive pressure in the channel 310 pushes against it as well as when a negative pressure in the channel 310 pulls the diaphragm 108 in the opposite direction. In this way, the strain gauge 515 is able to register both negative and positive pressure in the channel. By using a vacuum in this manner, it is possible for the pod 501 and diaphragm 108 to be separate from the transducer 503 such that, for example, the pod 501 can be a replaceable component and the transducer 503 can be a permanent component. This provides a mechanism for reducing costs of a system in which the use of a channel that must be replaced to ensure sterility—a sterile disposable component—can be made inexpensively while the more expensive transducer can be a non-replaceable component.

Note that the vacuum system includes a wall 520 of the pod 501 that provides a sealing surface 508 surrounding a recess 506 into which the transducer 503 cylindrical housing 511 fits to form a vacuum-tight seal so that a vacuum can be maintained between the diaphragm 108 and the outer surface of the force input plate 512. As a result of the vacuum-tight seal, only small amount of air needs to be drawn to maintain the vacuum permitting the use of a single vacuum line 284.

A vacuum applied to a vacuum line 284 draws air continuously from the minimal gap between the diaphragm 108 and the force input plate 512. The force input plate 512 may be rippled as indicated by undulations 514 to permit the force input plate 512 to flex more easily due to pressure, both negative and positive exerted by movement of the diaphragm.

Note that the transducer 503 may be used with any of the embodiments of FIGS. 6A through 7C as well as with the pressure pods that are described in '980.

FIGS. 8A through 8F show details of a pressure sensor 400 that includes a pod 402 and a transducer assembly 404. The pod 402 may be the same as the various pods described herein, for example, the pod 402 may have the configuration of the pod 501 illustrated in FIGS. 5A to 5C. It will be evident, however, that other configurations are also usable in the present embodiment. The pod 402 has a diaphragm 108 that is held in contact with a force input plate 421 of a sensor unit 418. The sensor unit 418 may be a transducer that generates a signal in response to detection of force. The force input plate 421 is held in contact with the diaphragm 108 of the connected pod by a vacuum supplied through an adapter 412. The adapter has a flange 423 that is used, in part, to preload, by means of a spring, the adapter 412 within a housing. The diaphragm 108 lies at the base of a well 413 surrounded by a wall 414 contacted by a seal 401 of the adapter 412, the seal being held against the wall 414 by the force of the vacuum. Thus the adapter seal 401 is highly flexible (for example, of silicone) and helps to maintain the vacuum between the pod 402 diaphragm 108 and the force input plate 421. The vacuum is applied to through the adapter 412 which supports and seals the sensor unit 418. The seal 401 may be of a resilient polymer such as silicone. Preferably the seal is shaped so that it can be compliant and flexible and such that air pressure presses it firmly against the wall 414 of the well 413 surrounding the diaphragm 108.

The vacuum source (such as a vacuum air pump, not shown) may be connected to a vacuum connector 406. A vacuum supply line 408 draws air from the space between the diaphragm 108 and the force input plate 421 through a bore inside the adapter 412, and therefore not visible in the drawings. The bore runs continuously through the adapter 412 from the vacuum supply line 408 to a bore opening 415. Thus, air is drawn through the bore opening 415 to maintain the vacuum. This maintains continuous contact between the diaphragm 108 and the force input plate 421 during pressure measurements even when the pressure in the channel 310 is negative. The adapter 412 has a hard end 417 that is seated on the perimeter of the diaphragm 108 by the vacuum force. The plane of the force input plate 421 is coplanar with a plane defined by the surface of the adapter 412 hard end 417.

The transducer assembly 404, includes the sensor unit 418 and the adapter 412. The transducer assembly 404 may be a permanent fixture, for example a component of a treatment machine, other types of fixed devices, and even non-treatment machines. The pod 402 may be a replaceable component and may be included as part of any of a fluid circuit. For example, see the discussion of FIG. 11 below. The connector 406 connects a vacuum supply line 408 to a vacuum source (not shown). The vacuum supply line 408 is connected to the adapter 412, which is a generally cylindrical member that holds a sensor unit 418. The adapter 412 has a bore through it that opens at an end thereof indicated at 414.

Figure 8A:
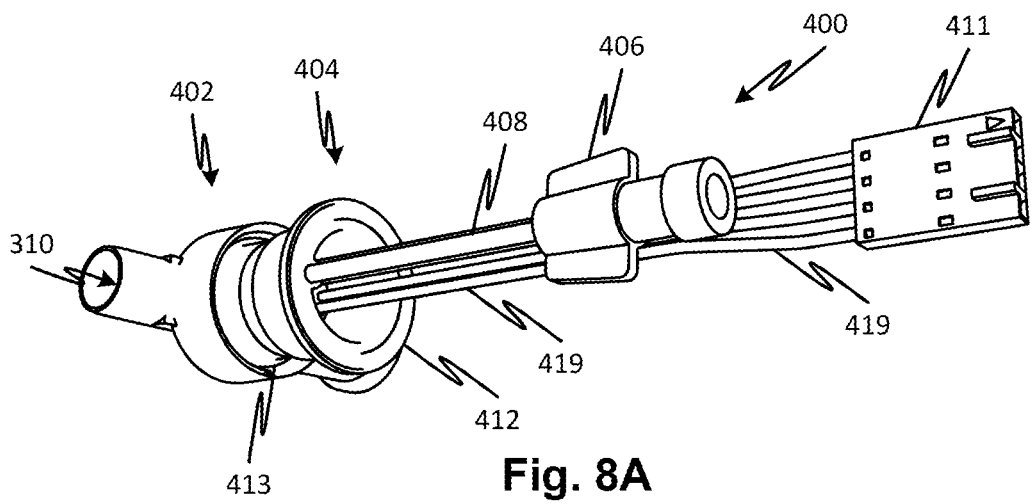
FIGS. 8A through 8H and 8J show details and different views of transducer that attaches to a pressure pod by means of a vacuum attachment system, according to embodiments of the disclosed subject matter.
Figure 8B:
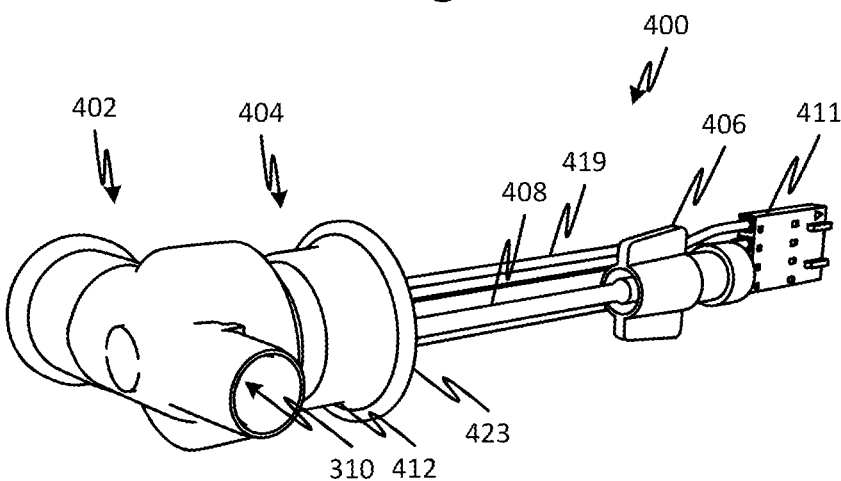
Figure 8C:
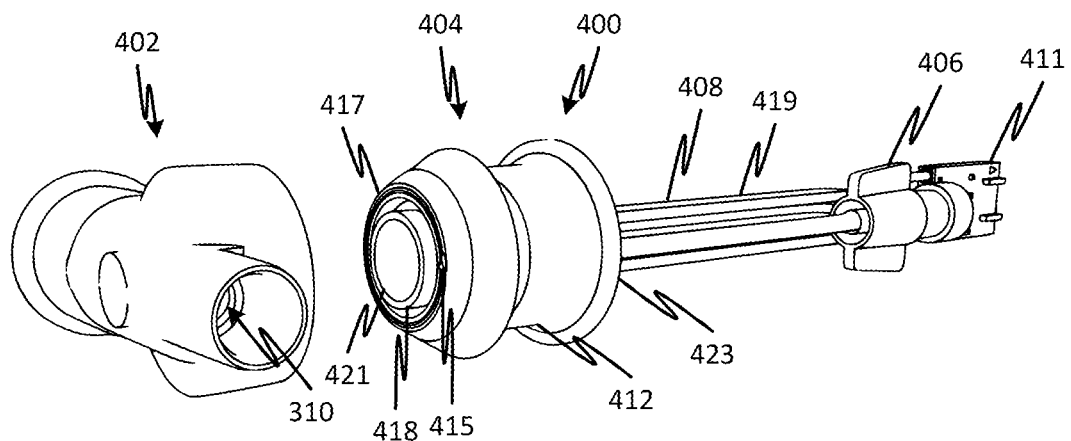
Figure 8D:
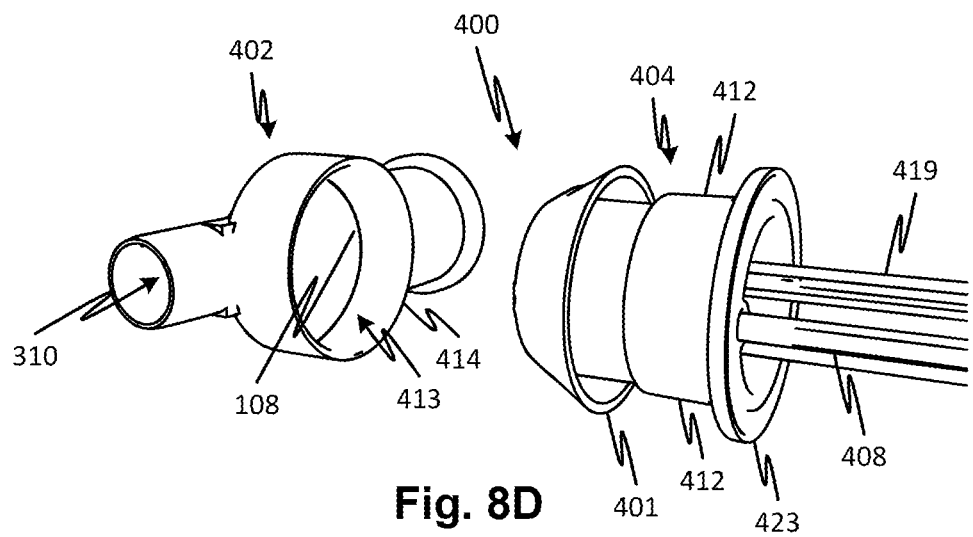
Figure 8E:
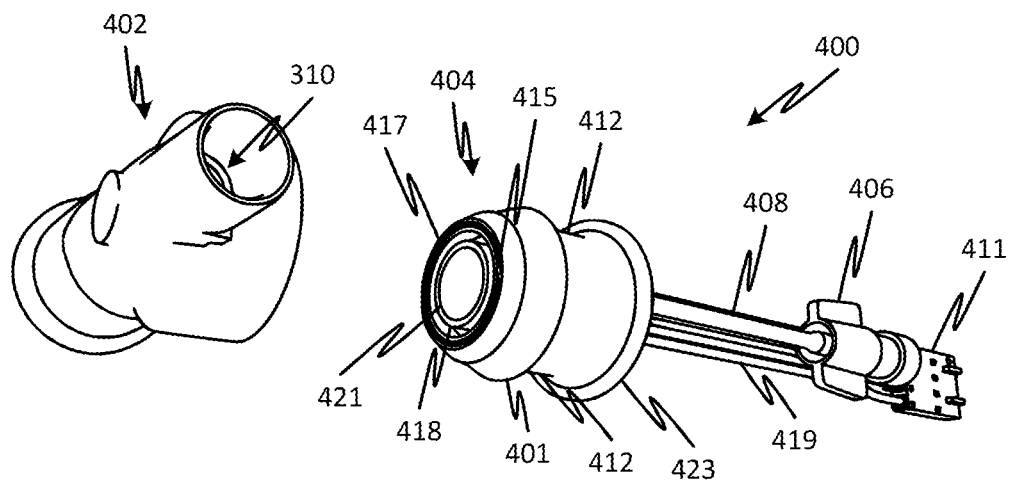
Figure 8F:
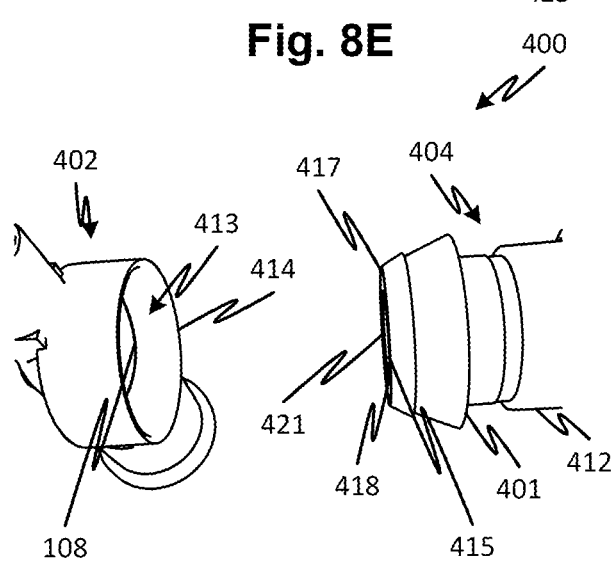
Figure 8G:
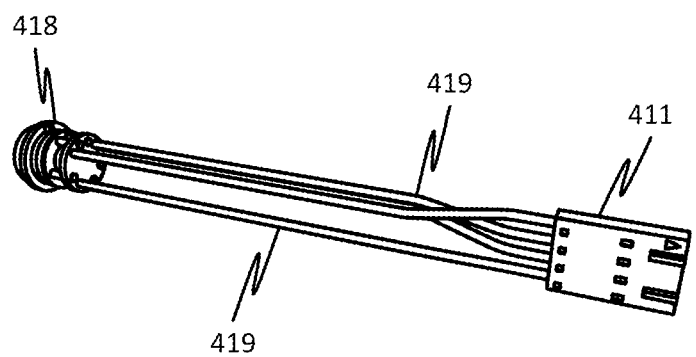
Figure 8H:
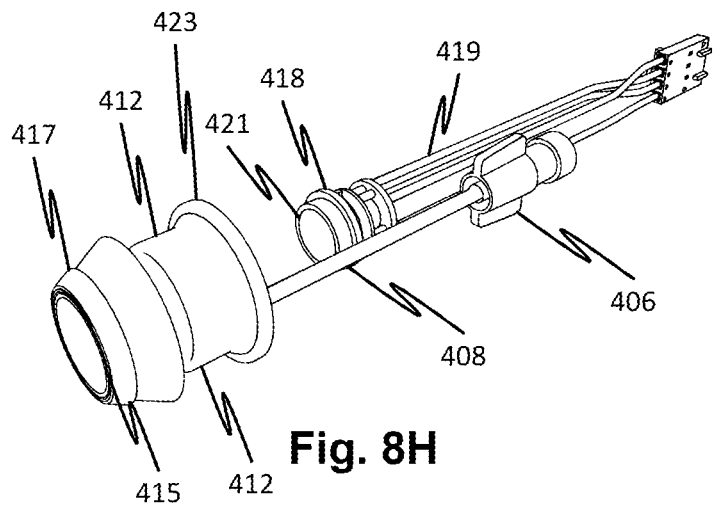
Figure 8J:
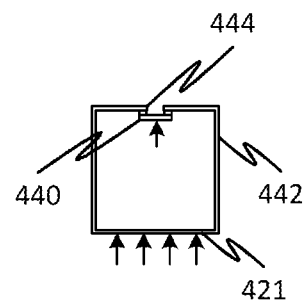

FIG. 8J shows a schematically a portion of the sensor unit. The sensor unit 418 may have a fluid-filled container 442 with the force input plate 421 on one end and a strain gauge 440, inside the container which has an opening 444 on an end opposite the force input plate on the other end. Thus, the strain gauge blocks the egress of fluid from the container 442 such that when the force input plate 421 is flexed it applies a negative or positive force to the strain gauge. The area of the force input plate 421 is relatively large and the area of the strain gauge is small such that the flexion of the force input plate 421 is limited. This constrains the amount of strain that is suffered by the force input plate and correspondingly by the diaphragm which limits the effect of creep on the response of the diaphragm. Thus, the force on the diaphragm is spread over a large area but the output transferred to the incompressible fluid is spread over a small area. Since the strain gauge itself is small any flexion in it is relatively large compared to the flex in the force input plate 421 so that the force input plate 421 displacement is reduced.

FIGS. 8C through 8F show the pod 402 ready to receive the transducer assembly 404 just prior to their mutual engagement which is shown if FIGS. 8A and 8B. FIG. 8G shows the sensor unit 418 alone and FIG. 8H shows the sensor unit 418 separated from the adapter 412. The sensor unit has electrical leads indicated at 419 which are terminated at an electrical connector 411.

Figure 9:
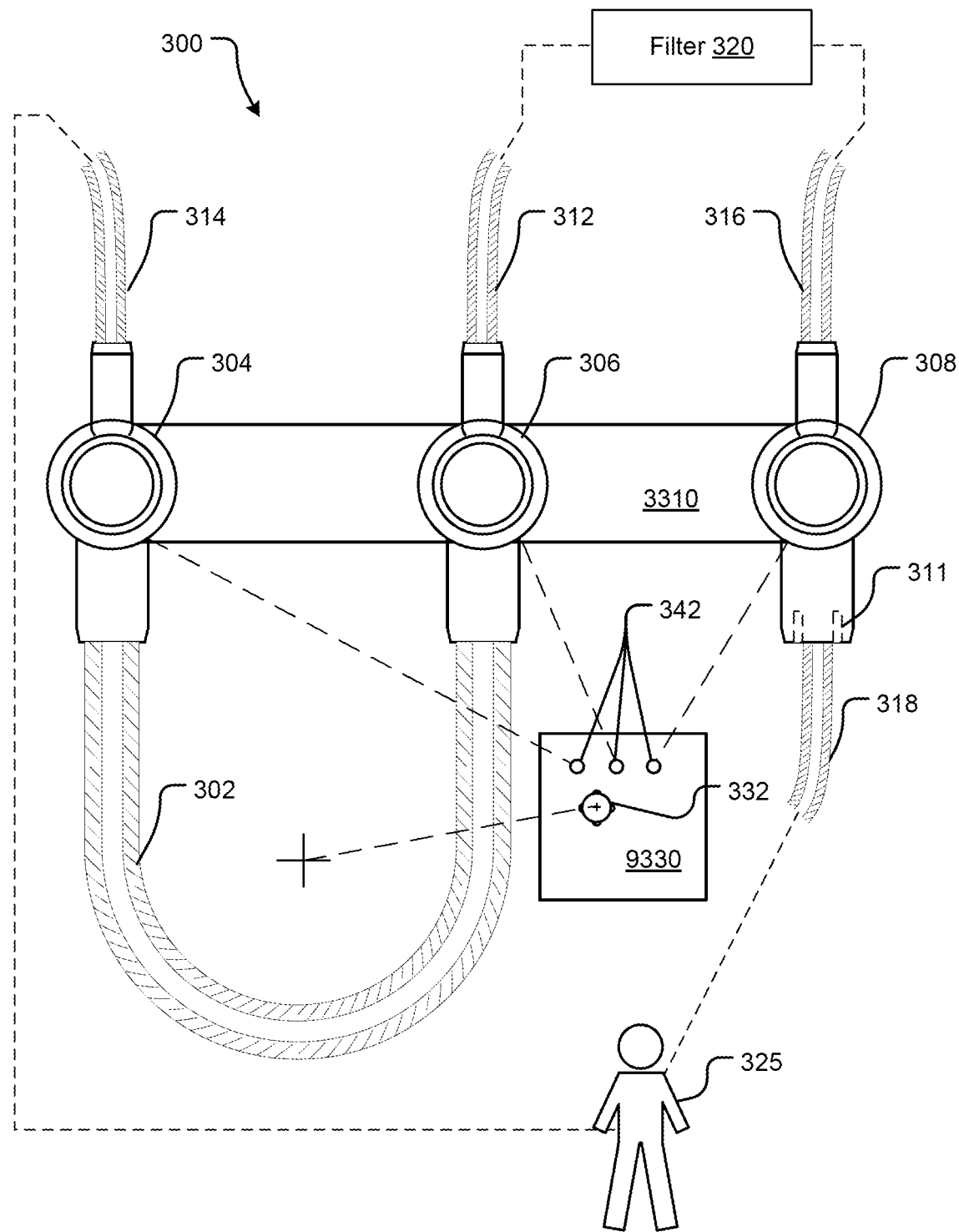
FIG. 9 shows an application of a fluid circuit with pressure pods integrated into it according to embodiments of the disclosed subject matter.
Figure 10A:
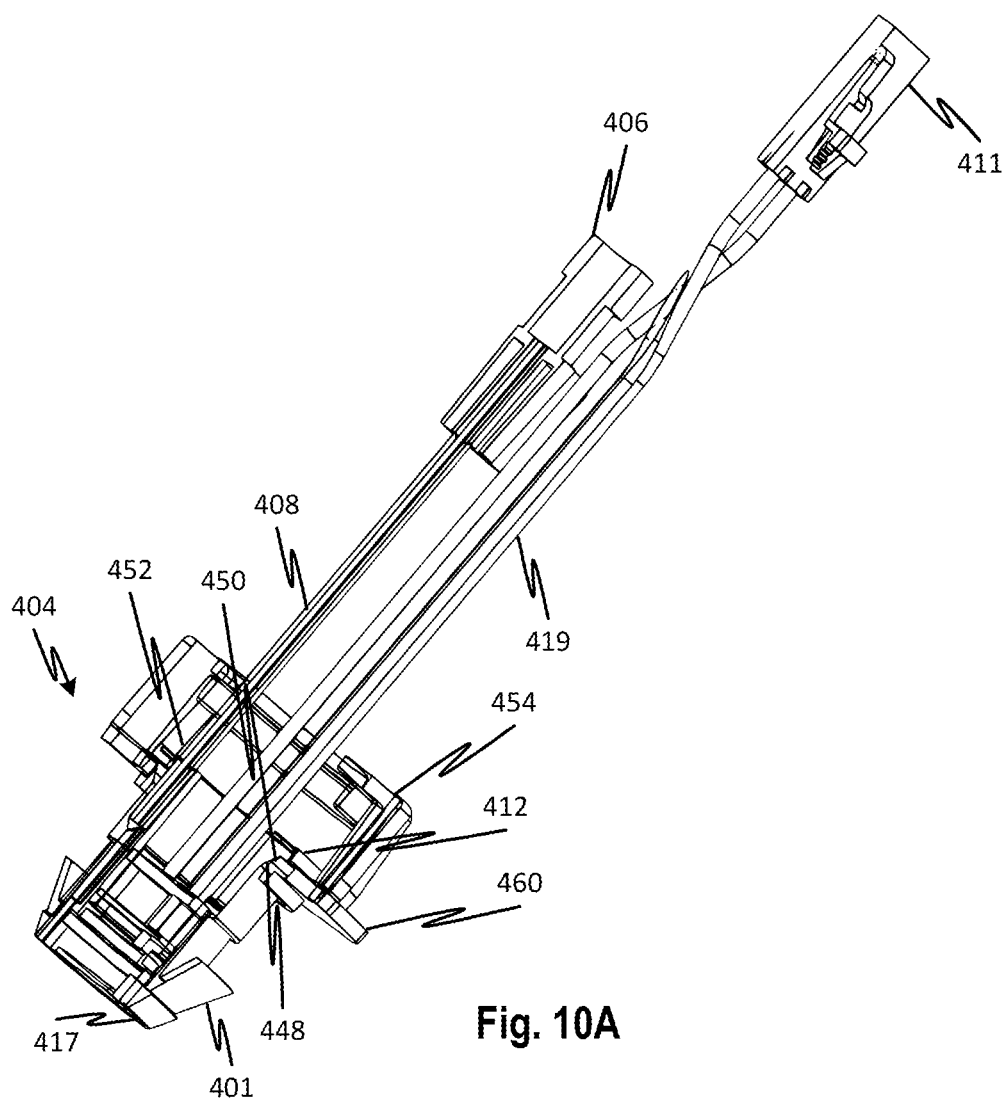
FIG. 10A is a section view of the pressure transducer according to embodiments of the disclosed subject matter.
Figure 10B:
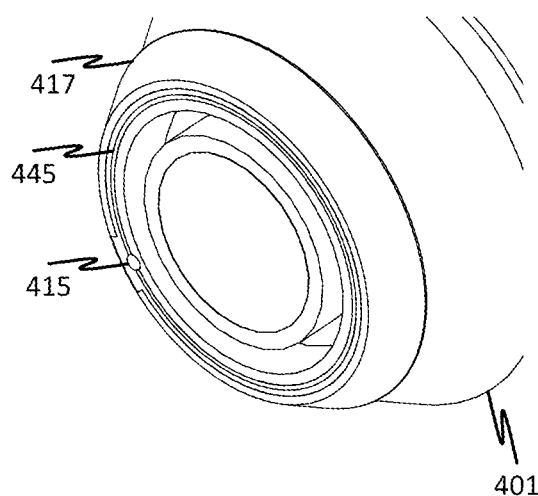
FIG. 10B shows a close-up of a hard end of the transducer adapter according to embodiments of the disclosed subject matter.
Figure 10C:
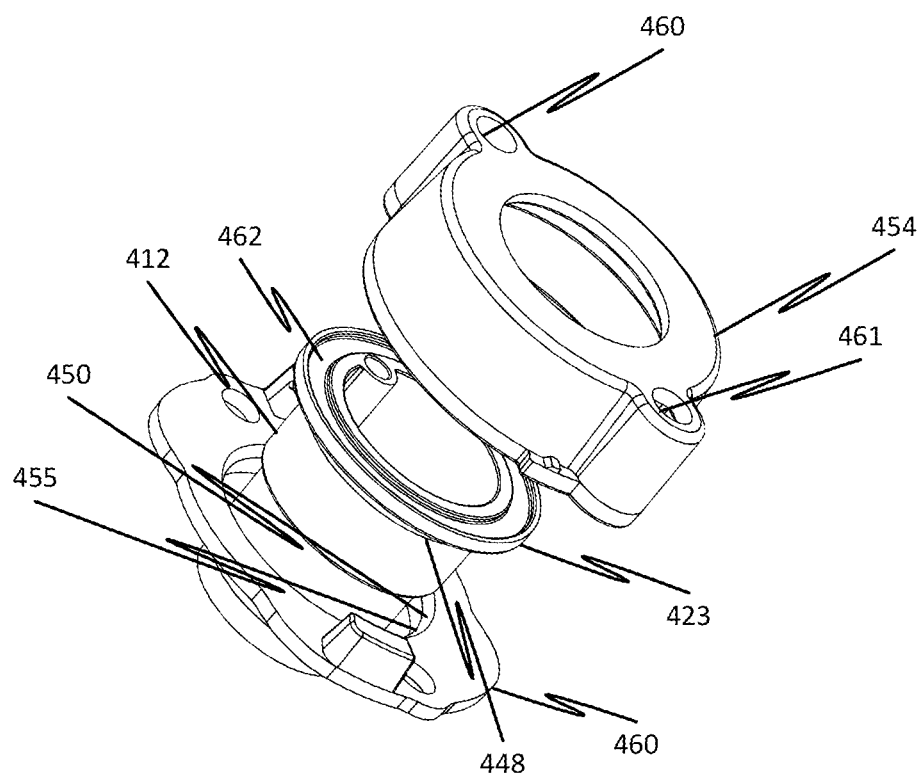
FIGS. 10C and 10D show oblique views of an enclosure that carries a spring and provides auto-location and freedom of movement of the pressure transducer according to embodiments of the disclosed subject matter.
Figure 10D:
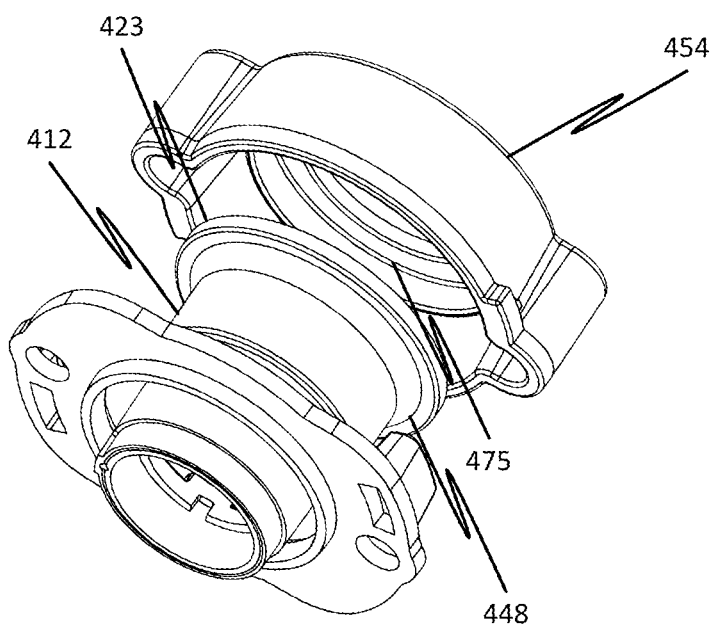

FIG. 9 shows a fluid circuit 300 with three pressure pods (fluid circuit portions as is 105) 304, 306, and 308 attached together by a single frame 3310. A pumping portion 302 and arterial blood line 314 and venous blood line 318, and pre- and post-filter lines 312 and 316 to and from filter 320, respectively, can be pre-attached so that the components can all be simultaneously positioned and attached to a treatment machine 9330. This attachment may connect all the pods 304, 306, and 308 with transducer fixtures 342 as well as a peristaltic pump actuator 332. The connections between arterial 314 and venous 318 blood lines are shown figuratively as is a patient 325. An adapter 311 may be provided to allow connection of small diameter tubes as required, in embodiments in which the pod chamber is the same size as one of the pins used to mold the pod. FIGS. 10A and 10B show components for fabricating a pressure pod according to embodiments of the disclosed subject matter. FIGS. 10C and 10D show stages in the manufacture of a pressure pod according to embodiments of the disclosed subject matter.

Note that the transducer fixtures 342 may correspond to any of the transducer embodiments disclosed herein, for example, they may include the transducer assembly 404. Thus, in this example, the attachment of the fluid circuit 300 with the transducer fixtures 342 may form three of the pressure sensors 400.

FIG. 10A shows a section view of the pressure sensor 400 and includes an enclosure 454 that holds a spring (not shown), within an annular space between the enclosure 454 and a base 460. Referring now also to FIGS. 10B through 10D, the spring nests in the annular recess 462 at one end and abuts a rim 475 in the enclosure 454 at the spring's other end. The spring may be a coil spring (not shown). The spring occupies an annular volume indicated at 452. The flange 423 is forced against the base 460 by the spring and the enclosure 454 holds the opposite end of the spring such that the flange 423 is urged toward the base until a beveled edge 448 on the inside of the flange nests, and is centered and held, by a conical surface 450 in the base. This arrangement makes the adapter 412 center itself with respect to the base when the pod 402 is not urged against it. An opening 455 in the base 460 is larger than the body of the adapter 412 so that it can float within the opening 455 and move around along axes perpendicular to the longitudinal axis of the pressure sensor 400. The freedom of movement allows the pod 402 and the hard end 417 to auto-locate with respect to each other when they are pushed together to engage the pod 402 and pressure sensor 400.

FIG. 10B shows the hard end 417 of the adapter 412 enlarged so that an annular recess 445 is visible. This spreads the vacuum suction applied through the bore opening 415 over a surface of the hard end 417 thereby maintaining contact between the force input plate 421 and the diaphragm 108. Mounting holes 461 allows the enclosure 454 to be bolted to a platform (not shown).

Figure 11:
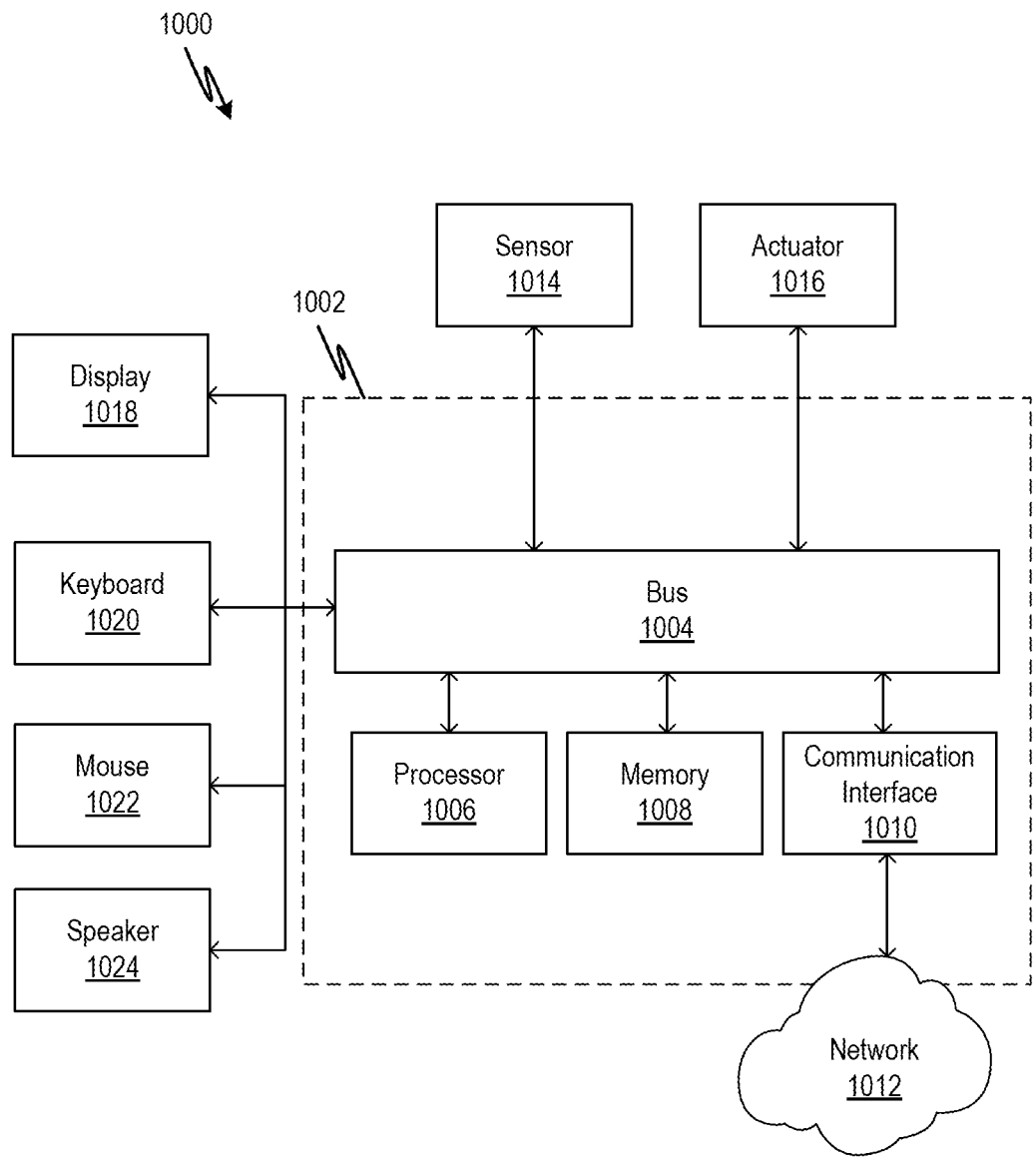
FIG. 11 is a block diagram of an example computer system 1000 portions or all of which may be incorporated in controllers disclosed herein, according to the disclosed embodiments.

FIG. 11 is a block diagram of an example computer system 1000 according to an embodiment. In various embodiments, all or parts of system 1000 may be included in a medical treatment device/system such as a renal replacement therapy system. In these embodiments, all or parts of system 1000 may provide the functionality of a controller of the medical treatment device/systems. In some embodiments, all or parts of system 1000 may be implemented as a distributed system, for example, as a cloud-based system.

System 1000 includes a computer 1002 such as a personal computer or workstation or other such computing system that includes a processor 1006. However, alternative embodiments may implement more than one processor and/or one or more microprocessors, microcontroller devices, or control logic including integrated circuits such as ASIC.

Computer 1002 further includes a bus 1004 that provides communication functionality among various modules of computer 1002. For example, bus 1004 may allow for communicating information/data between processor 1006 and a memory 1008 of computer 1002 so that processor 1006 may retrieve stored data from memory 1008 and/or execute instructions stored on memory 1008. In one embodiment, such instructions may be compiled from source code/objects provided in accordance with a programming language such as Java, C++, C#, .net, Visual Basic™ language, LabVIEW, or another structured or object-oriented programming language. In one embodiment, the instructions include software modules that, when executed by processor 1006, provide renal replacement therapy functionality according to any of the embodiments disclosed herein.

Memory 1008 may include any volatile or non-volatile computer-readable memory that can be read by computer 1002. For example, memory 1008 may include a non-transitory computer-readable medium such as ROM, PROM, EEPROM, RAM, flash memory, disk drive, etc. Memory 1008 may be a removable or non-removable medium.

Bus 1004 may further allow for communication between computer 1002 and a display 1018, a keyboard 1020, a mouse 1022, and a speaker 1024, each providing respective functionality in accordance with various embodiments disclosed herein, for example, for configuring a treatment for a patient and monitoring a patient during a treatment.

Computer 1002 may also implement a communication interface 1010 to communicate with a network 1012 to provide any functionality disclosed herein, for example, for alerting a healthcare professional and/or receiving instructions from a healthcare professional, reporting patient/device conditions in a distributed system for training a machine learning algorithm, logging data to a remote repository, etc. Communication interface 1010 may be any such interface known in the art to provide wireless and/or wired communication, such as a network card or a modem.

Bus 1004 may further allow for communication with a sensor 1014 and/or an actuator 1016, each providing respective functionality in accordance with various embodiments disclosed herein, for example, for measuring signals indicative of a patient/device condition and for controlling the operation of the device accordingly. For example, sensor 1014 may provide a signal indicative of a viscosity of a fluid in a fluid circuit in a renal replacement therapy device, and actuator 1016 may operate a pump that controls the flow of the fluid responsively to the signals of sensor 1014.

According to first embodiments, the disclosed subject matter includes a method of pressure measurement that includes determining a Moire pattern resulting from an interference of a Moire filter with markings on a diaphragm of a pressure pod. The method includes determining a movement or deformation of the diaphragm based on the Moire pattern and determining a fluid pressure in the pressure pod based on the movement or deformation of the diaphragm.

In variations thereof, the first embodiments include ones in which the Moire filter comprises concentric transparent and opaque circles. In variations thereof, the first embodiments include ones in which diaphragm has concentric transparent and opaque circles. In variations thereof, the first embodiments include ones in which the markings on the diaphragm are engraved or embossed.

According to second embodiments, the disclosed subject matter includes a method of pressure measurement, the method including determining a Moire pattern resulting from an interference of a Moire filter with markings on a protrusion on a diaphragm of a pressure pod. The method includes determining a movement of the protrusion on the diaphragm based on the Moire pattern and determining a fluid pressure in the pressure pod based on the movement of the protrusion on the diaphragm.

In variations thereof, the second embodiments include ones in which the Moire filter comprises parallel transparent and opaque lines. In variations thereof, the second embodiments include ones in which the markings on the protrusion on the diaphragm comprise parallel transparent and opaque lines. In variations thereof, the second embodiments include ones in which the markings on the protrusion on the diaphragm are engraved or embossed.

According to third embodiments, the disclosed subject matter includes a method of pressure measurement that includes determining a first Moire pattern resulting from an interference of a first Moire filter with markings on a diaphragm of a pressure pod. The method includes determining a movement or deformation of the diaphragm based on the first Moire pattern. The method includes determining a second Moire pattern resulting from an interference of a second Moire filter with markings on a protrusion on the diaphragm of the pressure pod. The method includes determining a movement of the protrusion on the diaphragm based on the second Moire pattern and determining a fluid pressure in the pressure pod based on the movement or deformation of the diaphragm and the movement of the protrusion on the diaphragm.

In variations thereof, the third embodiments include ones in which the first Moire filter comprises concentric transparent and opaque circles. In variations thereof, the third embodiments include ones in which markings on the diaphragm comprise concentric transparent and opaque circles. In variations thereof, the third embodiments include ones in which the markings on the diaphragm are engraved or embossed. In variations thereof, the third embodiments include ones in which the second Moire filter comprises parallel transparent and opaque lines. In variations thereof, the third embodiments include ones in which the markings on the protrusion on the diaphragm comprise parallel transparent and opaque lines. In variations thereof, the third embodiments include ones in which the markings on the protrusion on the diaphragm are engraved or embossed.

In variations thereof, any of the embodiments include ones in which the pressure pod includes a housing with a flow channel, the housing having a single wall forming a self-supporting structure with a defined flow channel connecting two ports in communication with the flow channel and the channel has one wall portion of the housing that is substantially thinner than a remainder of the housing, the one wall portion having a major dimension that is no larger than one of the two ports, thus permitting the housing to be closed by a molding operation and without requiring the attachment of separate parts to close the housing, the one wall portion comprising the diaphragm.

In variations thereof, any of the embodiments include ones in which the one wall portion is circular. In variations thereof, the any embodiments include ones in which the one wall portion is integral with the remainder of the housing. In variations thereof, the any embodiments include ones in which the one wall portion is configured such that the flow channel housing can be closed with a single molding operation and without requiring the attachment of separate parts to close the housing. In variations thereof, any of the embodiments include ones in which the ports are located on opposite sides of the channel with axes that are parallel to a major plane of the one wall portion. In variations thereof, any of the embodiments include ones in which the method is performed by an optical detector detecting a displacement of the one wall portion corresponding to negative as well as positive pressure within the channel. In variations thereof, any of the embodiments include ones in which the pressure pod is manufactured by providing first and second major mold parts having recesses defining major parts of the housing, inserting pins in the first and second major mold parts, the pins being shaped to define the flow channel of the pressure pod, one of the pins having a major face that defines an internal surface of the diaphragm, closing the first and second major mold parts with the pins therebetween and injection molding the housing and removing the pressure pod from the mold parts and withdrawing the pins from flow channel.

In variations thereof, any of the embodiments include ones in which the removing opens ports in the housing that communicate through the housing. In variations thereof, any of the embodiments include ones in which one of the pins has a major dimension that is larger than, equal in size to, the diaphragm. In variations thereof, any of the embodiments include ones in which one of the pins has a major dimension that is larger than, equal in size to, a diameter of the diaphragm. In variations thereof, any of the embodiments include ones in which the diaphragm has a projection on an outside surface thereof, the projection comprising the protrusion.

In variations thereof, any of the first embodiments include ones in which the method is performed by a controller of a system for measuring pressure in a fluid circuit. The system includes the pressure pod and an optical displacement measuring apparatus against which the pressure pod is immobilized, wherein the diaphragm is optically monitored by the optical displacement measuring apparatus.

In variations thereof, any of the first embodiments include ones in which the optical displacement measuring apparatus is configured to generate a signal responsively to displacement of the diaphragm, wherein the diaphragm is configured to present a smooth internal surface to an internal flow path of the pressure pod, the internal flow path extending between the access of inlet and outlet ports of the pressure pod having a hydraulic diameter of no more than 15 mm at all points therethrough.

In variations thereof, any of the first embodiments include ones in which an internal flow path of the pressure pod has a cross-section whose aspect ratio does not exceed three.

In variations thereof, any of the first embodiments include ones in which the system comprises a housing that is a self-supporting inline pod structure.

In variations thereof, any of the first embodiments include ones in which an internal surface of a flow path in the pressure pod has a positive or neutral draft from any point toward at least one of an inlet port and an outlet port of the pressure pod and at all of said internal surface from said any one point to said at least one of the inlet port and the outlet port.

In variations thereof, any of the first embodiments include ones in which the housing, including the diaphragm and the protrusion, are integral and of the same material such that they are configured to be molded as a single element.

In variations thereof, any of the first embodiments include ones in which one of the ports is larger than the other, and the larger port is connected to a fluid circuit for medical treatment, wherein the larger port is connected to a pump tubing segment and the other port is connected to a non-pump tubing segment.

In variations thereof, any of the first embodiments include ones in which the housing has an annular rim and the optical displacement measuring apparatus has a boss configured to mate with the annular rim.

In variations thereof, any of the first embodiments include ones in which the flow path from port to port has a hydraulic diameter that varies by not more than 80%.

In variations thereof, any of the first embodiments include ones in which the hydraulic diameter in the flow path remains at all points along the flow path, in a range between 4 mm and 10 mm.

In variations thereof, any of the first embodiments include ones in which the flow includes a blood flow.

According to fourth embodiments, the disclosed subject matter includes a pressure detection apparatus with a pressure pod having a chamber through which fluid flows and a diaphragm at the blind end of a recess with an access defined by a round ring, the diaphragm defining a wall of the chamber. A pressure transducer plug has a generally cylindrical wall with a vacuum channel formed therein and a resilient seal around a perimeter that forms a seal with an interior surface of the recess between the blind end and the access.

In variations thereof, the fourth embodiments include ones in which the plug has a flexible wall that touches the diaphragm. In variations thereof, the fourth embodiments include ones that further include a vacuum pump connected to the vacuum channel. In variations thereof, the fourth embodiments include ones in which the channel opens to a space between the flexible wall and the diaphragm such that the vacuum applied to the channel causes the flexible wall and the diaphragm to be held together and to flex together responsively to a pressure of fluid in the chamber.

According to fifth embodiments, the disclosed subject matter includes a pressure measurement apparatus with a pressure pod having a fluid channel defined in part by a diaphragm. The diaphragm is flat and is positioned in the base of a well that fits snugly over a pressure transducer plug, the transducer plug having a force input plate that lies adjacent the diaphragm when the well is fitted snugly over the pressure transducer plug. The pressure transducer plug has a bore connectable to a vacuum pump, the bore opening between the diaphragm and the force input plate such that air can be evacuated from a space between the force input plate and the diaphragm. A resilient seal surrounds the plug and is positioned and shaped to form a seal with the well. The pressure transducer plug has a rigid ring portion that is seated at a perimeter of the diaphragm when air is evacuated from a space between the force input plate and the diaphragm. A surface of the rigid ring portion being coplanar with a surface of the force input plate and a surface of the diaphragm.

In variations thereof, the fifth embodiments include ones in which the pressure transducer plug has a strain gauge to which force is applied by said force input plate through an incompressible fluid contained by said pressure transducer plug.

In variations thereof, the fifth embodiments include ones in which an area of the strain gauge is smaller than an area of the force input plate.

In variations thereof, the fifth embodiments include ones in which the bore opens at said rigid ring portion.

In variations thereof, the fifth embodiments include ones that further include a vacuum pump connected to said bore.

In variations thereof, the fifth embodiments include ones in which the pressure transducer plug includes a pressure transducer and a cylindrical adapter, the adapter having the bore and rigid ring portion, the pressure transducer having the force input plate.

In variations thereof, the fifth embodiments include ones in which the pressure pod is part of a disposable fluid circuit.

In variations thereof, the fifth embodiments include ones in which the diaphragm applies a negative force to said force input plate when a negative pressure is present in said fluid channel the negative force being responsive to a vacuum applied by said vacuum pump.

According to sixth embodiments, the disclosed subject matter includes a pressure measurement apparatus with a pressure pod having a fluid channel defined in part by a diaphragm. The diaphragm is flat and is positioned over a pressure transducer plug and held in place by a vacuum, the transducer plug having a force input plate that lies adjacent the diaphragm. The pressure transducer plug has a bore connectable to a vacuum pump, the bore opening between the diaphragm and the force input plate such that air can be evacuated from a space between the force input plate and the diaphragm. A resilient seal surrounds the plug and is positioned and shaped to form a seal with the diaphragm. The pressure transducer plug having a rigid ring portion that is seated at a perimeter of the diaphragm when air is evacuated from a space between the force input plate and the diaphragm. A surface of the rigid ring portion is coplanar with a surface of the force input plate and a surface of the diaphragm.

In variations thereof, the sixth embodiments include ones in which the pressure transducer plug has a strain gauge to which force is applied by said force input plate through an incompressible fluid contained by said pressure transducer plug.

In variations thereof, the sixth embodiments include ones in which an area of the strain gauge is smaller than an area of the force input plate.

In variations thereof, the sixth embodiments include ones in which the bore opens at said rigid ring portion.

In variations thereof, the sixth embodiments include ones that further include a vacuum pump connected to said bore.

In variations thereof, the sixth embodiments include ones in which the pressure transducer plug includes a pressure transducer and a cylindrical adapter, the adapter having the bore and rigid ring portion, the pressure transducer having the force input plate.

In variations thereof, the sixth embodiments include ones in which the pressure pod is part of a disposable fluid circuit.

In variations thereof, the sixth embodiments include ones in which the diaphragm applies a negative force to said force input plate when a negative pressure is present in said fluid channel the negative force being responsive to a vacuum applied by said vacuum pump.

According to seventh embodiments, the disclosed subject matter includes a method for measuring pressure. The method includes seating a diaphragm of a fluid channel against a force input plate, the seating including applying a vacuum to a space between the force input plate and the diaphragm. The method further includes drawing the force input plate toward the fluid channel by applying a negative pressure in said fluid channel, said drawing being responsive to a force of said vacuum. The method includes applying a force to a strain gauge through a fluid medium by means of said drawing the force input plate.

In variations thereof, the seventh embodiments include ones in which the seating includes inserting the force input plate into a well with the diaphragm at its base.

In variations thereof, the seventh embodiments include ones in which the applying a vacuum includes sealing a gap between the well and a support plug to which said force input plate is attached by means of a resilient sealing member that surrounds said support plug.

In variations thereof, the seventh embodiments include ones in which the support plug contains said fluid medium.

It will be appreciated that the modules, processes, systems, and sections described above can be implemented in hardware, hardware programmed by software, software instruction stored on a non-transitory computer readable medium or a combination of the above. For example, a method for measuring pressure can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of digital control systems sensors and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, pressure measurement devices, methods, and systems including control system which may include programmable processors and related effecters. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

Furthermore, certain features of the disclosed embodiments may sometimes be used to advantage without a corresponding use of other features. Accordingly, Applicants intend to embrace all such alternatives, modifications, equivalents, and variations that are within the spirit and scope of the present disclosure.

What is claimed is:

1. A method of pressure measurement comprising:
    determining a first Moire pattern resulting from an interference of a first Moire filter with markings on a diaphragm of a pressure pod;
    determining a movement or deformation of the diaphragm based on the first Moire pattern;
    determining a second Moire pattern resulting from an interference of a second Moire filter with markings on a protrusion on the diaphragm of the pressure pod;
    determining a movement of the protrusion on the diaphragm based on the second Moire pattern; and
    determining a fluid pressure in the pressure pod based on the movement or deformation of the diaphragm and the movement of the protrusion on the diaphragm.

2. The method of claim 1, wherein the first Moire filter comprises concentric transparent and opaque circles.

3. The method of claim 1, wherein the markings on the diaphragm comprise concentric transparent and opaque circles.

4. The method of claim 1, wherein the markings on the diaphragm are engraved or embossed.

5. The method of claim 1, wherein the second Moire filter comprises parallel transparent and opaque lines.

6. The method of claim 1, wherein the markings on the protrusion on the diaphragm comprise parallel transparent and opaque lines.

7. The method of claim 1, wherein the markings on the protrusion on the diaphragm are engraved or embossed.

* * * * *